US012678022B2

(12) United States Patent
Tyan et al.

(10) Patent No.: US 12,678,022 B2
(45) Date of Patent: Jul. 14, 2026

(54) APPARATUSES AND METHODS INVOLVING MULTI-MODAL IMAGING OF A SAMPLE

(71) Applicant: SRI International, Menlo Park, CA (US)

(72) Inventors: Jenn-Kwei Tyan, Princeton, NJ (US); Michael Raymond Piacentino, Robbinsville, NJ (US)

(73) Assignee: SRI International, Menlo Park, CA (US)

( * ) Notice: Subject to any disclaimer, the term of this patent is extended or adjusted under 35 U.S.C. 154(b) by 878 days.

(21) Appl. No.: 17/435,318

(22) PCT Filed: Mar. 1, 2020

(86) PCT No.: PCT/US2020/020565
§ 371 (c)(1),
(2) Date: Aug. 31, 2021

(87) PCT Pub. No.: WO2020/180755
PCT Pub. Date: Sep. 10, 2020

(65) Prior Publication Data
US 2022/0125280 A1     Apr. 28, 2022

Related U.S. Application Data

(60) Provisional application No. 62/812,405, filed on Mar. 1, 2019, provisional application No. 62/812,413, filed on Mar. 1, 2019.

(51) Int. Cl.
*A61B 1/00* (2006.01)
*A61B 1/05* (2006.01)
*A61B 1/06* (2006.01)

(52) U.S. Cl.
CPC .... *A61B 1/000094* (2022.02); *A61B 1/00006* (2013.01); *A61B 1/000095* (2022.02);
(Continued)

(58) Field of Classification Search
CPC ........ A61B 1/000094; A61B 1/000095; A61B 1/00006; A61B 1/00096; A61B 1/05; A61B 1/0646
See application file for complete search history.

(56) References Cited

U.S. PATENT DOCUMENTS

2002/0007123 A1*  1/2002  Balas ................... A61B 1/0646
                                                          600/431
2002/0093655 A1   7/2002  Everett et al.
                  (Continued)

OTHER PUBLICATIONS

Qi et al. "Polarized multispectral imaging in a rigid endoscope based on elastic light scattering spectroscopy," Biomed. Opt. Express 3, 2087-2099 (2012).
(Continued)

*Primary Examiner* — Michael J Carey
*Assistant Examiner* — William B Chou
(74) *Attorney, Agent, or Firm* — Dicke, Billig & Czaja, PLLC

(57) ABSTRACT

An example apparatus includes a light source, first and second polarizers, an image sensor, a filter, and control circuitry. The light source outputs a light beam, and the first polarizer passes first polarized light from the output light beam and toward a sample. The image sensor collects light reflected from the sample responsive to the passed first polarized light. The second polarizer passes second polarized light from the reflected light and toward the image sensor. The filter selectively passes the reflected light in a visible light range and near infrared range (NIR) light range toward the image sensor. The control circuitry causes the first and second polarizers to adjust to different polarization angles, and collects the image data of the sample from the reflected light.

21 Claims, 28 Drawing Sheets

(52) U.S. Cl.
    CPC ............ *A61B 1/00096* (2013.01); *A61B 1/05*
                    (2013.01); *A61B 1/0646* (2013.01)

(56)                      References Cited

U.S. PATENT DOCUMENTS

| | | | |
|---|---|---|---|
| 2002/0171831 | A1 | 11/2002 | Backman et al. |
| 2003/0040668 | A1* | 2/2003 | Kaneko ................ A61B 1/0646 |
| | | | 600/407 |
| 2004/0240712 | A1 | 12/2004 | Rowe et al. |
| 2007/0263226 | A1 | 11/2007 | Kurtz et al. |
| 2009/0075391 | A1 | 3/2009 | Fulghum, Jr. |
| 2015/0381909 | A1* | 12/2015 | Butte ................. A61B 1/00045 |
| | | | 250/578.1 |
| 2018/0000401 | A1* | 1/2018 | Kang ..................... A61B 1/063 |
| 2018/0066931 | A1 | 3/2018 | Swanson |
| 2018/0132706 | A1* | 5/2018 | Nagae ................ A61B 1/00006 |
| 2018/0284417 | A1* | 10/2018 | Deisseroth ......... G02B 21/0012 |
| 2018/0344137 | A1* | 12/2018 | Themelis .............. G06T 11/001 |

OTHER PUBLICATIONS

International Search Report of related PCT Application No. PCT/
US2020/020565 dated Jun. 11, 2020.

\* cited by examiner

APPARATUSES AND METHODS INVOLVING MULTI-MODAL IMAGING OF A SAMPLE

INCORPORATION BY REFERENCE

This Utility Patent Application claims priority under 35 U.S.C. § 371 to International Application Serial No. PCT/US2020/020565, filed Mar. 1, 2020; which claims the benefit of U.S. Provisional Patent Application No. 62/812,405, filed Mar. 1, 2019; and U.S. Provisional Patent Application No. 62/812,413, filed Mar. 1, 2019; which are both incorporated herein by reference in their entirety.

OVERVIEW

Surgical interventions can help surgeons avoid damaging or misidentifying soft tissues, especially nerves, resulting in serious patient injury. Currently, there is no clinical system available that can assist surgeons to identify the important soft tissues in a safe, specific, and real-time manner during surgery or other for other applications.

SUMMARY

The present invention is directed to overcoming the above-mentioned challenges and others related to a multi-modal imaging of a sample, such as an object and/or plurality of objects in the sample.

Various embodiments of the present disclosure are directed to apparatuses, devices and methods thereof that can be used for concurrently providing visible and near infrared (NIR) polarized images of a sample and/or an object in real-time using different polarization light.

Specific embodiments are directed to an apparatus including a light source, first and second polarizers, an image sensor, a filter, and control circuitry. The light source outputs a light beam along an optical pathway. The first polarizer is coupled to the light source, and can pass first polarized light from the output light beam and toward a sample along the optical pathway. The image sensor, which includes circuitry, collects light reflected from the sample in response to the passed first polarized light. The second polarizer is arranged along the optical pathway between the sample and the image sensor, and can pass second polarized light from the reflected light and toward the image sensor. The first and second polarizers are linear and cross each other, such as with either an orthogonal or slant direction. The filter is arranged along the optical pathway and can selectively pass the reflected light in a visible light range and NIR light range (or wavelengths) toward the image sensor. The filter can include a first bandpass filter to selectively pass visible wavelengths or light and a second bandpass filter to selectively pass NIR wavelengths or light. In other embodiments and/or in addition, the filter includes a bandpass filter to selectively block incident light and a color filter array to capture NIR, red, green, and blue channels.

The control circuitry is configured and arranged with the image sensor to image the sample by causing the first polarizer and the second polarizer to adjust (or shift) to different polarization angles with respect to one another, and by collecting image data of the sample from the reflected light while the first and second polarizers are at the different polarization angles with respect to one another and while the filter selectively passes the visible light and the NIR light ranges of the second polarized light. The sample can include, in specific embodiments, a tissue sample which has or includes soft tissue.

The first and second polarized light are associated with a slant or an angle with respect to the other. The control circuitry can cause the first polarizer and the second polarizer to adjust to the different polarization angles, resulting in optical reflections of birefringence from portions of the tissue sample to be focused or discriminated when aligned to a polarization of collimated incident light. For example, the control circuitry collects the image data by causing the filter to selectively pass the visible light and the NIR light and by collecting a plurality of image frames of the sample while the first and second polarizers are at the different polarization angles with respect to one another, and while the filter selectively passes the visible light range and while the filter selectively passes the NIR light range. In a number of embodiments, the control circuitry collects the image data by capturing first image data using collimated incident light as generated by the first and second polarizer and by capturing second image data using non-polarized light from the light source. The captured first and second image data can include image frames and/or video of the sample.

In various embodiments, the control circuitry collects a sequential order of image frames responsive to the first and second polarizers being at the different polarization angles with respect to one another and while the filter selectively passes both the NIR and visible light ranges. That apparatus can further include motorized rotators arranged with the first and second bandpass filters, and the control circuitry can selectively rotate the motorized rotator such that one of the first and second bandpass filters are arranged in the optical pathway to selectively pass one of the visible light and NIR light. For example, a first motorized rotator is coupled to the first polarizer and a second motorized rotator is coupled to the second polarizer, and the control circuitry selectively rotates the first and second motorized rotators such that the first and second polarizers are at the different polarization angles. The first and second polarizers can each include a plurality of polarized filters arranged on the first and second motorized rotators to provide the different polarization angles. Each of the first and second polarizers can include an all-pass filter arranged on the first and the second motorized rotators, the all-pass filters being configured to pass light of all polarizations. However, embodiments are not so limited and the polarizers can be adjusted or shifted by other means, such as electric and/or magnetic polarization, or other mechanical movements, such as a slide projector-type mechanism in which the slides include different polarizers.

In other embodiments and/or in addition, the control circuitry (and/or an additionally coupled processing circuitry) can generate an NIR image frame and a visible light image frame from the image data collect while the first and second polarizers are at the different polarization angles and fuses the NIR image frame and visible light image frame into a single image view. The apparatus can further include processing circuitry in communication with the control circuitry. The processing circuitry can revise the image data to improve image contrast of areas of interest (e.g., soft tissues) in the image data of the sample, identify locations of the areas of interest in the revised image data, and combine a plurality of polarized NIR image frames and a plurality of polarized visible light image frames, collected as the image data, into a single composite image of the sample based on the revised image data and the identified locations of the areas of interest.

In a number of specific embodiments, the processing circuitry can provide feedback to the control circuitry. For example, the processing circuitry identifies which of the different polarization angles of the first and second polarizers results in areas of interest of the sample being in focus, and provides feedback to the control circuitry to revise the image data based on the areas of interest being in focus.

Various embodiments are directed to methods of using the above-described apparatus. An example method includes adjusting a first polarizer and a second polarizer to different polarization angles with respect to one another, wherein the first and second polarizers are linear and cross each other and while at each of the different polarization angles, and outputting a light beam along an optical pathway using a light source. The method further includes passing first polarized light, using the first polarizer, from the output light beam and toward a sample along the optical pathway, reflecting light from the sample responsive to the first polarized light, and passing second polarized light, using the second polarizer, from the reflected light and toward an image sensor. The second polarized light can be selectively passed in a visible light range and a NIR light range toward the image sensor. The method additionally includes collecting, using the image sensor, image data of the sample from the reflected light while the first and second polarizers are at the different polarization angles with respect to one another and while the visible light and the NIR light ranges of the second polarized light are selectively passed.

Collecting the image data can include causing a filter to selectively pass the visible light range and the NIR light range, and collecting a plurality of image frames of the sample while the first and second polarizers are at the different polarization angles with respect to one another, while the filter selectively passes the visible light range, and while the filter selectively passes the NIR light range. For example, the method includes collecting a sequential order of image frames responsive to the first and second polarizers being at the different polarization angles with respect to one another, and while a filter selectively passes both the NIR and visible light ranges. In other embodiments and/or in addition, the method further includes capturing first image data using collimated incident light as generated by the first and second polarizer, and capturing second image data using non-polarized light from the light source. The captured first and second image data can include image frames and/or video of the sample.

In various embodiments, the method includes generating an NIR image and a visible image from the image data collected while the first and second polarizers are at the different polarization angles, and fusing the NIR image and visible image into a single image. For example, collecting the image data can include capturing a plurality of NIR image frames and a plurality of visible light image frames while the first and second polarizers are at the different polarization angles, and the method further includes fusing together the plurality of NIR image frames and the plurality of visible light image frames into a single optimized image.

In some embodiments, adjusting the first polarizer and the second polarizer to the different polarization angles results in optical reflections of birefringence from portions of the sample to be focused or discriminated when aligned to polarization of collimated incident light. The method can further include identifying which of the different polarization angles of the first and second polarizers results in an area of interest of the sample being in focus.

A number of embodiments are directed to a non-transitory computer-readable storage medium comprising instructions that when executed cause processing circuitry of a computing device to receive image data of a sample or an object, the image data including a plurality of polarized NIR image frames and a plurality of polarized visible light image frames of the sample collected using a plurality of different polarization angles of illumination light and imaging light. The instructions are further executed to revise the image data to improve image contrast of areas of interest in the image data of the sample, to identify locations of the areas of interest in the image data, and to combine the plurality of polarized NIR image frames and the plurality of polarized visible light image frames into a single composite image of the sample based on the revised image data and the identified locations of the areas of interest. The illumination light and the imaging light can include a plurality of first polarized light and a plurality of second polarized light that are crossed with each other and for the plurality of different polarization angles.

The instructions to revise the image data can be executed to adjust a contrast of the image data and, thereby, increase salient features of the sample. For example, the instructions to adjust the contrast of the plurality of polarized visible light image frames are executed to, convert red, green, blue channels of the plurality of polarized visible light image frames to luma (Y), blue-difference (Cb), and red-difference (Cr) color spaces, and to compute a plurality of histograms, each histogram corresponding to the Y color space of a section of the plurality of polarized visible light image frames. The instructions are further executed to, based on the plurality of histograms, redistribute light intensity values in the plurality of polarized visible light image frames, apply a bilateral filter to the Y color space of the plurality of polarized visible light image frames, combine the redistributed light intensity values with the bilateral filtered Y color space based on local energy of the respective section, and convert the combined Y color space, along with unchanged versions of the Cb and Cr color space to the red, green, and blue channels. Local energy, as used herein, refers to or includes a response of a pixel region, which can be obtained using gradient-based filtering.

In a number of embodiments, the instructions to adjust the contrast of the plurality of polarized NIR image frames are executed to compute a plurality of histograms, each histogram corresponding to light intensity values in a section of the plurality of polarized NIR image frames, and based on the plurality of histograms, to redistribute the light intensity values in the plurality of polarized NIR image frames. The instructions are further executed to apply a bilateral filter to the light intensity values of the plurality of polarized NIR image frames, and to combine the redistributed light intensity values with the bilateral filtered light intensity values based on local energy of the respective section.

The instructions to adjust the contrast of the plurality of image frames can further be executed to align the image data, including aligning the plurality of polarized NIR image frames with the plurality of polarized visible light image frames. As a specific example, the instructions to align the image data are executed to, for alignment of two image frames of the plurality of polarized NIR image frames and the plurality of polarized visible light image frames, identify keypoints in each of the two image frames, identify shape descriptors of features of the sample by dividing boundaries of shapes, use the shape descriptors to sort keypoints between the two image frames based on a measure of similarity to the boundaries, estimate a homography using the sorted keypoints to match keypoints between the two image frames, and use the homography estimate to align pixels in the two image frames and output the aligned image frames.

The instructions to revise the image data to improve image contrast can further be executed to combine the plurality of polarized visible image frames to form a composite visible image, combine the plurality of polarized NIR image frames to form a combined NIR image, and combine the composite visible image with the composite NIR image to form the single composite image. For example, the instructions to combine the plurality of polarized NIR image frames and the plurality of polarized visible light image frames into the single composite image of the sample can be executed to use the aligned image frames to generate the single composite image that enhances contrast and color channels compared to the plurality of polarized NIR image frames and the plurality of polarized visible light image frames.

In further embodiments, the instructions to adjust the contrast of the image data are further executed to generate a pyramid transform for the each of the plurality of polarized NIR image frames and the plurality of polarized visible image frames, and to determine, using each pyramid transform, a match measure based on local normalized correlation at each sample position and salience measures based on local region energy. The instructions are further executed to generate a composite pyramid from the pyramid transforms by selecting salient component patterns from the pyramid transforms based on the sample positions in which the salience measures are different, and generate the composite image through inverse pyramid transform based on the composite pyramid.

The instructions to identify locations of the areas of interest in the image data are executed to identify potential areas of interest using a training set of annotations in sample images, and systematically modify the training set for a plurality of different conditions. For example, the training set for soft tissue can be augmented by transforming a training image from one domain to another domain.

In specific and related embodiments, the instructions to identify the locations of the areas of interest are executed to generate a feature map having anchors in the plurality of polarized visible light image frames and the plurality of polarized NIR image frames using different size anchor windows (where each anchor includes a boundary of the respective image frame likely to contain a respective feature), to generate, for each anchor of the feature map, an anchor classification and probability of each anchor containing the respective feature, and to select based on the probability and refine the location and size to fit over the respective feature. The instructions can be further executed to resize each of the anchors of the feature map to a fixed size, generate revised anchor classifications and a revised probability of each anchor containing the respective feature, identify final anchors including identification of the features having boundaries based on the revised probabilities, and output the final anchors as restored to an original size and location corresponding to the image frame. The instructions can be further executed to generate image masks for the final anchors, the image masks being configured to hide portions of the image frames and to reveal other portions that include the feature.

In specific embodiments, the instructions are further executed to provide feedback to image sensor used to collect the image data based on the single composite image, the feedback being indicative of a subset of the plurality of different polarization angles of the illumination light and imaging light. For example, the instructions are executed to track changes in feature characteristics using the single composite image and image masks for the final anchors, compare energy of the features in the plurality of polarized NIR image frames and the plurality of polarized visible image frames using the single composite image. The instructions are further executed to, based on the comparison, select the most significant image frames from among the plurality of polarized NIR image frames and the plurality of polarized visible image frames which contribute to the energy of the composite image, and output feedback data to the image sensor. The feedback data can include an optimized polarization set based on the most significant image frames for guiding the image sensor for the particular features. For example, the feedback data includes an optimized set of angles of polarization for the illumination light and the imaging light based on the single composite image and object segmentation, and which is provided to the image sensor that collects the image data.

Various-related and more specific embodiments are directed to an apparatus which includes an image sensor arranged with control circuitry, and processing circuitry. The image sensor configured and arranged with control circuitry to collect image data of a sample, the image data including a plurality of polarized NIR image frames and a plurality of polarized visible light image frames captured using a plurality of different polarization angles of illumination light and imaging light. The processing circuitry revises the image data to improve image contrast of areas of interest in the image data of the sample, to identify locations of the areas of interest in the image data, and to combine the plurality of polarized NIR image frames and the plurality of polarized visible light image frames into a single composite image of the sample based on the revised image data and the identified locations of the areas of interest. The processing circuitry can provide feedback data to the control circuitry based on the single composite image, the feedback data being indicative of a subset of the plurality of different polarization angles of the illumination light and imaging light.

In specific embodiments, the apparatus further includes a light source, first and second polarizers, and a filter. The light source outputs a light beam along an optical pathway. The first polarizer is coupled to the light source and can pass first polarized light from the output light beam and toward the sample along the optical pathway. The second polarizer is arranged along the optical pathway between the sample and the image sensor, and passes second polarized light from the reflected light and toward the image sensor, wherein the first and second polarizers are linear and cross each other. The filter is arranged along the optical pathway, and selectively passes the reflected light in a visible light range and a NIR light range toward the image sensor. The image sensor collects light reflected from the sample in response to the passed reflected light. The control circuitry is configured and arranged with the image sensor to image the sample by causing the first polarizer and the second polarizer to shift or adjust to the different polarization angles with respect to one another, and by collecting image data of the sample from the reflected light while the first and second polarizers are at the different polarization angles with respect to one another and while the filter selectively passes the visible light and the NIR light ranges of the second polarization.

However embodiments are not so limited. For example, the light source and the image sensor can include a plurality of light sources and a plurality of image sensors. The control circuitry is configured and arranged with the plurality of image sensors to image the sample by causing the plurality of image sensors to capture image data of the sample using the illumination light and imaging light of the different polarization angles with respect to one another, and by collecting image data of the sample from the plurality of image sensors. Additionally, although the above describes imaging of a sample, embodiments are not so limited and can include imaging of a whole or partial objects.

Embodiments in accordance with the present disclosure include all combinations of the recited particular embodiments. Further embodiments and the full scope of applicability of the invention will become apparent from the detailed description provided hereinafter. However, it should be understood that the detailed description and specific embodiments, while indicating preferred embodiments of the invention, are given by way of illustration only, since various changes and modifications within the spirit and scope of the invention will become apparent to those skilled in the art from this detailed description. All publications, patents, and patent applications cited herein, including citations therein, are hereby incorporated by reference in their entirety for all purposes.

BRIEF DESCRIPTION OF THE DRAWINGS

Various example embodiments can be more completely understood in consideration of the following detailed description in connection with the accompanying drawings, in which.

Figure 1:
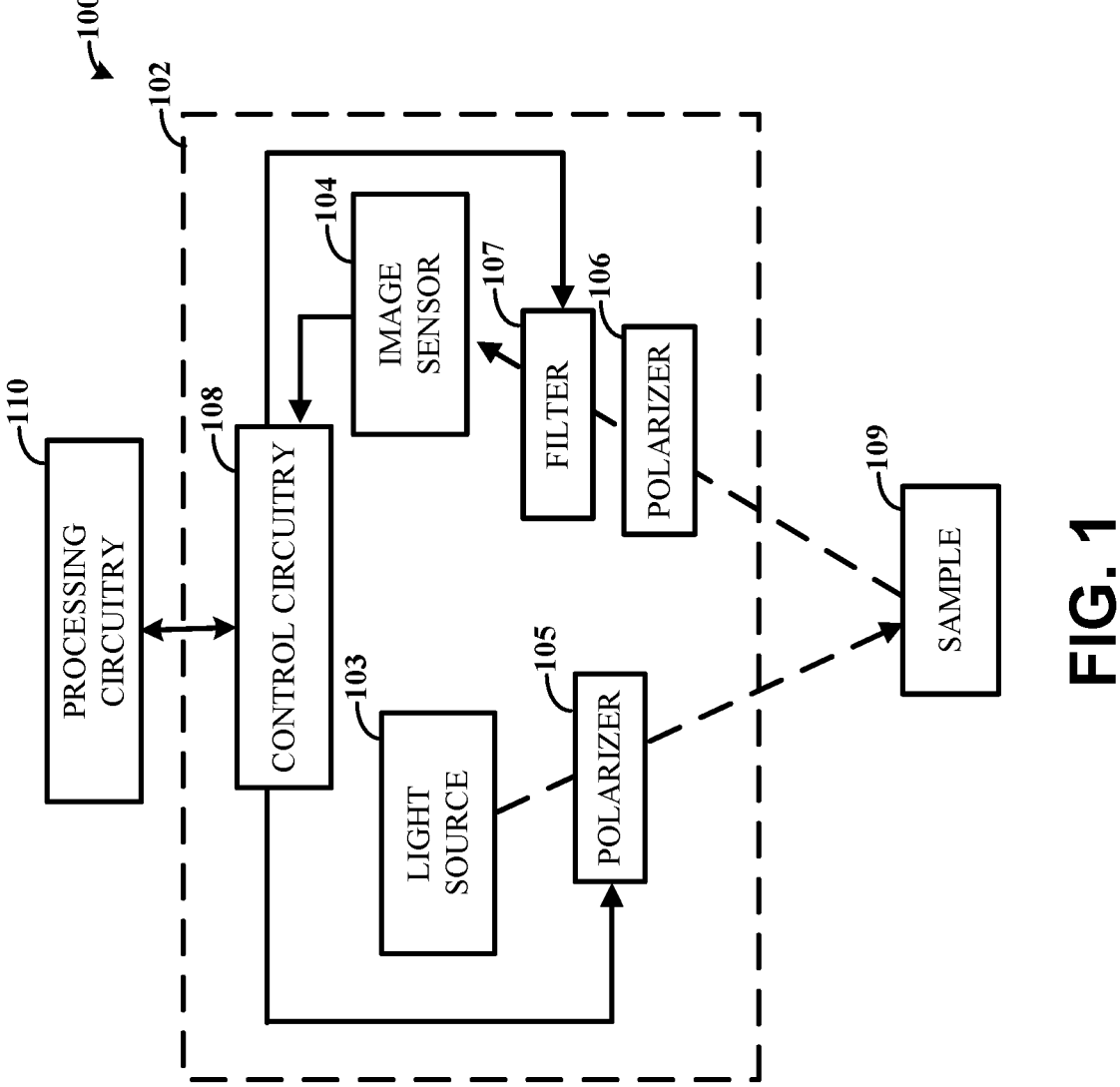
FIG. 1 illustrates an example of an apparatus for imaging, in accordance with various embodiments.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION

Aspects of the present disclosure are believed to be applicable to a variety of imaging apparatus and methods involving imaging an object and/or a sample using multiple imaging modalities. In specific embodiments, the imaging apparatus concurrently images an object in real-time using polarized near infrared light and polarized visible light. While the present invention is not necessarily limited to such applications, various aspects of the invention may be appreciated through a discussion of various embodiments using this context.

Accordingly, in the following description various specific details are set forth to describe specific embodiments presented herein. It should be apparent to one skilled in the art, however, that one or more other examples and/or variations of these embodiments can be practiced without all the specific details given below. In other instances, well known features have not been described in detail so as not to obscure the description of the embodiments herein. For ease of illustration, the same reference numerals can be used in different diagrams to refer to the same elements or additional instances of the same element.

An imaging apparatus can be used for real-time imaging of soft tissue, such as for medical images of soft tissues highlighted for surgery (including but not limited to vessels, nerves and membranes) or other visualization applications. The imaging apparatus can visualize soft tissue by integrating information from different yet complementary modalities, such as visible light, NIR light, and ultrasonic waves. The imaging apparatus integrates visible and near infrared (NIR) information with polarization under different orientation angles. Multiple polarized images are taken from both the visible and NIR spectrums, and fused into a single image view. This single image view can be used to provide visualization information to guide a surgery in real time and with low latency, such as capturing the image data and providing a composite image in a range of 30-60 milliseconds. As used herein, NIR light or spectrum includes or refers light in the electromagnetic spectrum range of 715 nanometers (nm) to 2500 nm. Visible light or spectrum includes or refers to light in the electromagnetic spectrum range of 400 nm to 700 nm. The light used for imaging can include the full NIR spectrum and/or visible light spectrum or portions thereof.

NIR images may provide an advantage over using visible-range light alone, in that the NIR spectrum may provide deeper tissue penetration due to less absorption by hemoglobin and water. Additionally, soft tissue have special aspect ratios of tissue cells compared to other cells in the body. The aspect ratio of the soft tissue refers to the long and thin shapes of structures of the soft tissue, such as nerve and blood vessels, which can be difficult to visualize using visible light due to the shapes of the particular tissue. Using polarized NIR may result in a strong anisotropic interaction with light as the long and thin structures may be more sensitive to polarized light than visible light, resulting in stronger response signals than other undirected structures. The optical reflections of birefringence from soft tissues may be best intensified when aligned to the polarization of the collimated incident light. Embodiments in accordance with the present disclosure include an imaging apparatus that collects visible light images and NIR images of a sample and may identify when the soft tissues are aligned to the polarization. This identification can be used as feedback to the apparatus for reducing latency for subsequent images taken.

Embodiments in accordance with the present disclosure involve an apparatus including a light source, first and second polarizers, an image sensor, a filter, and control circuitry. The light source outputs a light beam along an optical pathway. The first polarizer is coupled to the light source and passes first polarized light from the output light beam and toward a sample along the optical pathway. The image sensor, which includes circuitry, collects light reflected from the sample in response to the passed first polarized light. The second polarizer is arranged along the optical pathway between the sample and the image sensor, and passes second polarized light from the reflected light and toward the image sensor. The first and second polarizers are linear and cross each other, such as with either an orthogonal or slant direction (e.g., polarization or orientation angles). The filter is arranged along the optical pathway and selectively passes the reflected light in a visible light range or wavelengths and NIR light range or wavelengths toward the image sensor. The filter can include a first bandpass filter to selectively pass visible light or wavelengths and a second bandpass filter to selectively pass NIR light or wavelengths. In other embodiments and/or in addition, the filter includes a bandpass filter to selectively block incident light and a color filter array to capture NIR, red, green, and blue channels.

The first and second polarized light are associated with a slant or an angle with respect to the other. The control circuitry causes the first polarizer and the second polarizer to adjust to the different polarization angles, resulting in optical reflections of birefringence from portions of the tissue sample to be focused or discriminated when aligned to a polarization of collimated incident light.

In some specific embodiments, the control circuitry collects a sequential order of image frames responsive to the first and second polarizers being at the different polarization angles with respect to one another and while the filter selectively passes both the NIR and visible light ranges. The apparatus can further include motorized rotators arranged with the first and second bandpass filters, and the control circuitry selectively rotates the motorized rotator such that one of the first and second bandpass filters are arranged in the optical pathway to selectively pass one of the visible light and NIR light (or wavelengths). For example, the first and second polarizers can each include a plurality of polarized filters arranged on the first and second motorized rotators to provide the different polarization angles. However, embodiments are not so limited and the polarizers can be shifted by other means, such as electric and/or magnetic polarization, or other mechanical movements, such as a slide projector-type device in which the slides include different polarizers.

In other embodiments and/or in addition, the control circuitry (and/or an additionally coupled processing circuitry) generates an NIR image frame and a visible light image frame from the image data collect while the first and second polarizers are at the different polarization angles and fuses the NIR image frame and visible light image frame into a single image view. The apparatus can further include processing circuitry in communication with the control circuitry. The processing circuitry revise the image data to improve image contrast of areas of interest (e.g., soft tissues) in the image data of the sample, identify locations of the areas of interest in the revised image data, and combine a plurality of polarized NIR image frames and a plurality of polarized visible light image frames into a single composite image of the sample based on the revised image data and the identified locations of the areas of interest.

In a number of specific embodiments, the processing circuitry provide feedback to the control circuitry. For example, the processing circuitry identifies which of the different polarization angles of the first and second polarizers results in areas of interest of the sample being in focus, and provides feedback data to the control circuitry to revise the image data based on the areas of interest being in focus.

Various embodiments are directed to methods of using the above described apparatus and/or computer-readable instructions which are executed to perform methods of using the above described apparatus. Additionally, although a number of embodiments are described herein as imaging a sample, embodiments are not so limited and include imaging apparatuses and methods of using imaging apparatuses for imaging a whole or part of an object.

Turning now to the figures, FIG. 1 illustrates an example of an apparatus for imaging, in accordance with various embodiments. The apparatus can be used for imaging of soft tissue using cross-angled polarized light, as further described herein.

The apparatus 100 can include an imaging device 102 that images a sample 109. The imaging device 102 includes a light source 103 that outputs a light beam along an optical pathway. The light source 103 can include a collimated light source, such as lasers, light emitting diodes (LEDs), and other light sources. The optical pathway can be from the light source 103 toward the sample 109 and reflected back to an image sensor 104. The sample 109 can include or be a tissue sample, such as from a patient, in specific embodiments.

Arranged along the optical pathway includes a first polarizer 105 and a second polarizer 106 which selectively pass light waves of a specific polarization and block light waves of other polarizations. The first polarizer 105 can be coupled to the light source 103, and passes first polarized light from the output light beam and toward the sample 109 along the optical pathway. The second polarizer 106 is along the optical pathway between the sample 109 and the image sensor 104, and passes second polarized light from the reflected light and toward the image sensor 104. The first and second polarizers 105, 106 can be linear and the first and second polarizations can cross one another, with either an orthogonal or slant direction. The first polarized light and second polarized light can be associated with a slant or angle (such as perpendicular in a specific embodiments) with respect to one another.

The first and second polarizers 105, 106 can have adjustable polarization angles, such that the polarizers can be adjusted or changed to different polarization angles with respect to one another. In some embodiments, the adjustment includes a physical rotation of the polarizers 105, 106. In other embodiments, the adjustment includes a change in the polarization angle caused by an electric field on a polarizer, sometimes referred to as electric polarization. The polarization angle, in such embodiments, can be changed to any specific degree with a strength and direction of the electric field.

A filter 107 is arranged along the optical pathway, and selectively passes the reflected light in a visible light range and a NIR light range toward the image sensor 104. The filter 107 can include a notch filter or a bandpass filter. As a specific example, the filter 107 includes a first bandpass filter to selectively pass visible light or wavelengths and a second bandpass filter to selectively pass NIR light or wavelengths. In further embodiments and/or in addition, the filter 107 can include a notch or bandpass filter to selectively block incident light and a color filter array used to capture NIR, red, green, and blue channels. In various specific embodiments, the apparatus 100 can further include a motorized rotator arranged with the first and second bandpass filters, and the control circuitry 108 selectively rotates the motorized rotator such that one of the first and second bandpass filters are arranged in the optical pathway to selectively pass one of the visible light and NIR light ranges or wavelengths. Example filters include a visible band filter, such as a 400-700 nm filter or a 410-690 nm filter, and a NIR band filter, such as a 715-2500 nm filter or a 715-1100 nm filter.

The image sensor 104, which includes circuitry, collects light reflected from the sample 109 in response to the passed first polarization light and second polarization light in the visible and/or MR light range or wavelengths. As further described herein, a plurality of images can be captured at each of the visible light range and the NIR light range, and while the first and second polarizers 105, 106 are at different angles. The image sensor 104 can include a multi-channel sensor, such as a multi-channel camera.

The image device 102 further includes control circuitry 108 arranged with the image sensor 104 and the first and second polarizers 105, 106 to control imaging of the sample 109. The control circuitry 108 can cause the first polarizer 105 and the second polarizer 106 to adjust to the different polarization angles with respect to one another, and to collect image data of the sample 109 from the reflected light while the first and second polarizers 105, 106 are at the different polarization angles with respect to one another and while the filter 107 selectively passes the visible light and the NIR light ranges of the second polarized light. In specific embodiments, the control circuitry 108 causes the first polarizer 105 and the second polarizer 106 to adjust to the different polarization angles, resulting in optical reflections of birefringence from portions of the tissue sample to be focused or discriminated when aligned to a polarization of collimated incident light.

In various embodiments, a plurality of NIR images and a plurality of visible light images, using different angled polarized light, can be collected. The control circuitry 108 can sequence through the different polarization angles for NIR images followed by visible light images, and in other embodiments, can collect an NIR image and a visible light image (prior to rotating to different polarized angles) and sequences through the different polarization angles. The number of different polarization angles sequenced through can vary across different embodiments and specific implementations. For example, a range of polarization angles can be used, such as a range of at least two angles and up to two hundred angles, although embodiments are not so limited and may include more angles, such as five hundred angles. In some specific embodiments, two polarization angles are used. In other embodiments, five or seven polarization angles are used. In further embodiments, twenty or fifty polarization angles are used. In some embodiments, the imaging apparatus can adjust the number of polarization angles. For example, the number of polarization angles can be changed by the imaging apparatus in real time, such as through the optimization process as described below. More polarization angles may allow for better visualization and/or imaging of the object, such as in a sample, while resulting in greater computation time for processing the images. The optimum number of polarization angles can be dependent on the particular object(s) being imaged and/or the application, and may be changed for imaging different object(s). For example, the control circuitry 108 collects the image data by causing the filter 107 to selectively pass the visible light and the NIR light (or wavelengths), and by collecting a plurality of image frames of the sample 109 while the first and second polarizers 105, 106 are at the different polarization angles with respect to one another, while the filter 107 selectively passes the visible light and while the filter 107 selectively passes the NIR light (or wavelengths). In other embodiments, the control circuitry 108 collects the image data by collecting a sequential order of image frames responsive to the first and second polarizers 105, 106 being at the different polarization angles with respect to one another, and while the filter 107 selectively and sequentially passes both the NIR and visible light ranges.

In various embodiments in which the polarizers 105, 106 are physically rotated, the apparatus 100 can further include a first motorized rotator coupled to the first polarizer 105 and a second motorized rotator coupled to the second polarizer 106. The control circuitry 108 selectively rotates the first and second motorized rotators such that the first and second polarizers are at the different polarization angles. The first and second polarizers 105, 106 can each include a plurality of polarized filters arranged on the first and second motorized rotators to provide the different polarization angles, with each of the first and second polarizers 105, 106 including an all-pass filter arranged on the first and the second motorized rotators. The all-pass filters can pass light of all polarizations. However, embodiments are not so limited and the filters can be physically rotated or changed in other ways. For example, the apparatus 100 can apply an electric field to the polarizers to change the polarization and/or the filters can be changed in other physical manners, such as a mechanism similar to a slide projector in which each polarizer includes a plurality of polarizer slides. As another example, the polarization angle can be changed by applying a magnetic field on a transparent optical element, such as a prism or ferrofluid, which changes the polarization angle.

In specific embodiments, the control circuitry 108 collects the image data by capturing first image data using collimated incident light as generated by the first and second polarizer 105, 106 and capturing second image data using non-polarized light from the light source 103. The non-polarized light can be used to capture an image that is used as a reference, which is compared to the other images captured using polarized light. Additionally, the reference (e.g., a reference image captured with non-polarized light) can be used as a baseline for fusing with the other images to form an optimal and/or enhanced image. In some specific embodiments, the captured first and second image data includes still image frames and/or video of the sample 109.

The apparatus 100 can further include processing circuitry 110 coupled to the imaging device 102. The processing circuitry 110 can be used to fuse the plurality of images together. For example, the processing circuitry 110 generates an NIR image frame and a visible light image frame from the image data collect while the first and second polarizers 105, 106 are at the different polarization angles and fuses the NIR image frame and visible light image frame into a single image view. In various embodiments, a plurality of NIR image frames and visible light image frames are captured and fused together. The processing circuitry 110 can provide feedback to the control circuitry 108. For example, the processing circuitry 110 identifies which of the different polarization angles of the first and second polarizers 105, 106 results in areas of interest of the sample 109 (e.g., particular soft tissue) being in focus, and provides feedback to the control circuitry 108 to revise the image data collected based on the areas of interest being in focus. The revision can include identification of a subset of the plurality of different polarization angles, such that subsequent images can be captured faster and using less processing resources as compared to capturing the images using the plurality of different polarization angles.

The processing circuitry 110 can revise the image data provided by the image sensor 104 and fuse the images together. For example, the processing circuitry 110 can improve the image contrast of areas of interest (e.g., soft tissues) in the image data of the sample 109, identify locations of the areas of interest in the revised image data, and combine a plurality of polarized NIR image frames and a plurality of polarized visible light image frames, collected as the image data, into a single composite image of the sample 109 based on the revised image data and the identified locations of the areas of interest. As may be appreciated, the processing circuitry 110 (sometimes referred to as "a processor") can be implemented as a multi-core processor or a processor circuit implemented as a set of processor circuits integrated as a chip set. The processing circuitry 110 can thereby include a single, or multiple computer circuits including memory circuitry for storing and accessing the firmware or program code to be accessed or executed as instructions to perform the related operation(s).

In various specific embodiments, the image device 102 can form part of an endoscope, however embodiments are not so limited. For example, the imaging device 102 can be used during surgery, in which the latency of providing the fused single image can be vital. Example surgeries include minimally invasive procedures operated by human surgeons or robotic surgeons/devices, such as spine surgery, cardiac surgery and cancer surgery, where soft tissue damage and malignant tumor identification are of great concern. In other embodiments, the imaging apparatus 100 is used for safe injection guidance of needle and syringe to help physicians visualize correct blood vessels. As specific example, the imaging apparatus 100 can be used for removal of breast cancer tissue, to mitigate incomplete resection and local recurrence. As another example, the imaging apparatus 100 can be used to provide feedback to mitigate nerve damage caused by various types of surgeries. The imaging apparatus 100 can allow the surgeon to see structures to be resected, such as malignant tumors, and structures that need to be avoided, such as blood vessels and nerves. Additionally, use of the imaging apparatus 100 during surgery can allow for performance of the operation without use of contrast dyes and/or agents. Using optical and ultrasonic responses based on tissue characteristics, the imaging apparatus 100 can combine multimodal imaging to provide a single image view with the necessity of visualization information to guide the surgery, and which can avoid or mitigate soft tissue damage or cancer tumor misidentification.

Figure 2B:
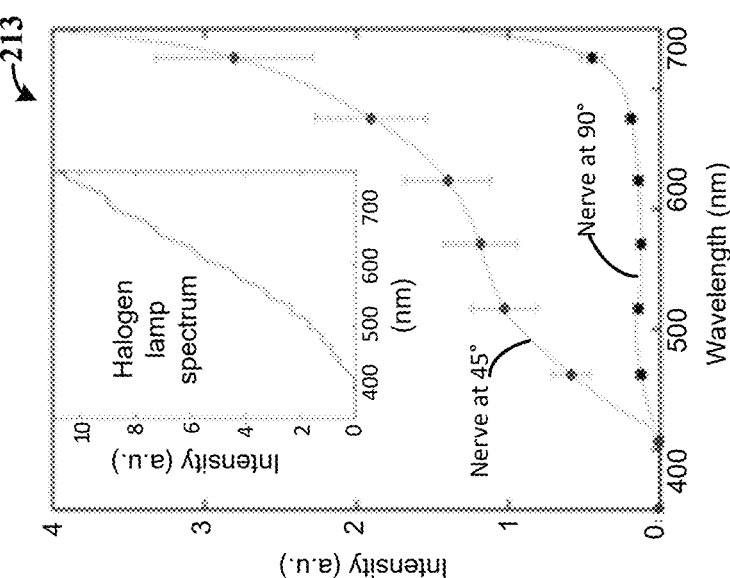
FIGS. 2A-2B illustrate another example imaging apparatus, in accordance with various embodiments.
Figure 2A:
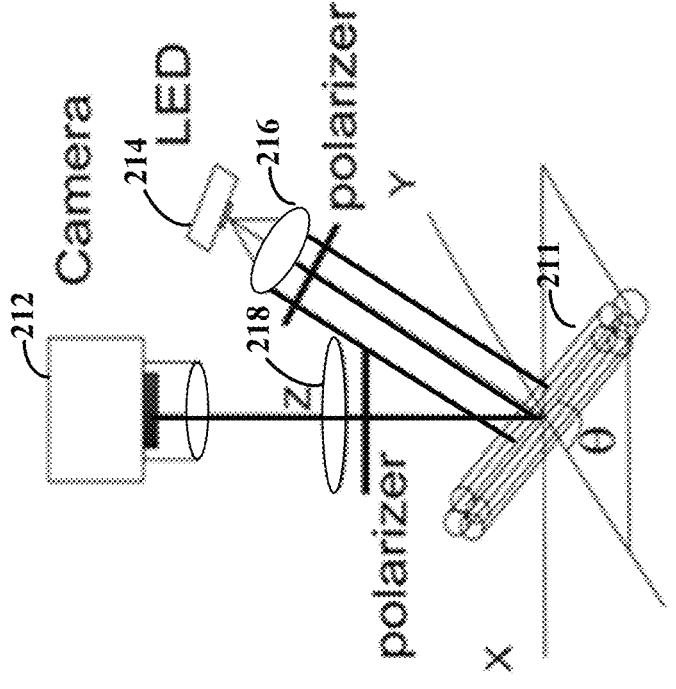

FIGS. 2A-2B illustrate another example imaging apparatus, in accordance with various embodiments. More specifically, FIG. 2A illustrates an example imaging apparatus that includes a collimated polarized light source 214 and an image sensor (e.g., a camera 212) to measure the reflected light with perpendicular polarization. The imaging apparatus can collect visible and NIR images of the image plane 211 with polarization. Two polarizers 216, 218 are placed in front of the camera 212 and light source 214 respectively, cross each other with either orthogonal or slant direction. The camera 212 can include a color filter array used to capture four channels (e.g., NIR, red, blue and green) at the same time. In other embodiments, notch filters (410-690 nm and 715-1100 nm) are alternatively used to separate visible band and NIR band imaging. An additional filter can be arranged with the lens of the camera 212 to block incident light.

Multiple visible or NIR images can be acquired by rotating both polarizers 216, 218 at the same time with different angle. As a non-limiting example, rotating both polarizers 216, 218 every thirty degree, six frames from visible band and six frames from NIR band for a scene can be obtained, respectively. These images can be processed by the image processing functions to produce an optimized view of the image for the scene. Such an imaging apparatus can be designed based on tissue structures and alternatively apply polarization at multiple orientations to acquire the images where soft tissues responded the best.

FIG. 2B is a graph 213 that illustrates an example of anisotropic optical properties of thin slices of nervous-tissue model which is measured using polarized light microscopy in transmission mode. The refraction of transmitted light through a nerve is a function of wavelength, where the nerve tissue reveals an enhanced red shifted transmission intensity when oriented to forty-five degrees with respect to the cross-polarizers. This phenomenon is consistent for all the different wavelengths and the tissue intensity is amplified as the wavelength increased. A NIR camera with 700-900 nm wavelength can filter out other tissue areas and results in the best response for nerve signals. Such an imaging apparatus can be designed based on tissue structures and alternatively apply polarization at different orientations to acquire the images where soft tissues responded the best.

Figures 3A, 3B:
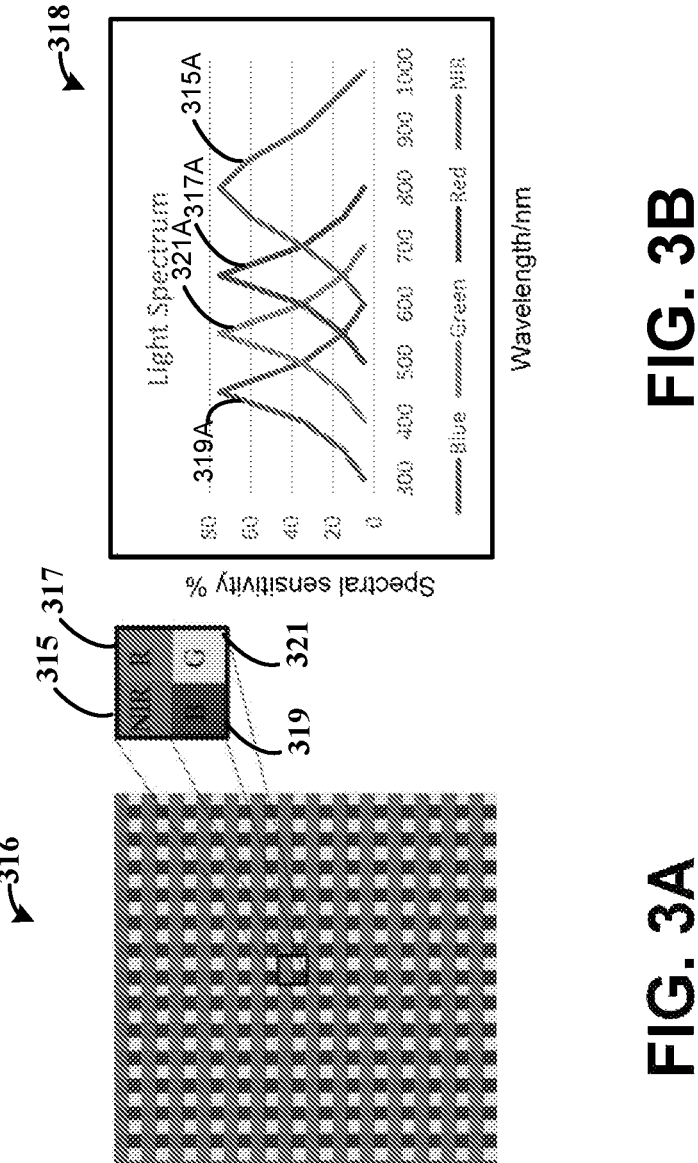
FIGS. 3A-3B illustrate an example color filter, in accordance with the present disclosure.

FIGS. 3A-3B illustrate an example color filter, in accordance with the present disclosure. An image sensor (e.g., a camera) can include a color filter array used to capture visible light images and NIR images at the same time. The image sensor can have four or more channels (e.g., NIR, red, green, and blue). In various embodiments, the notch filters may not be switched to collect visible and NIR images separately. The image sensor can further include a notch filter in front of the lens to block incident light. With the synchronized polarization, the image sensor can capture videos/images in real time. In some embodiments, the image sensor captures videos and/or images with and without polarization based on the given lighting condition (e.g., an LED) in real time. Four images, R, G, B, and NIR, are extracted from the corresponding channels in the raw image. The polarized signal can be extracted from the two images captured with and without polarization illumination, such as two NIR images captured with and without polarization illumination. Compared to other systems addressing the special lighting issue in an operation room, the imaging apparatus, as described herein, can be very simple and uses a compact way of providing high sensitivity in detecting soft tissue signal(s). The imaging system can capture color reflectance and NIR images in real time, with the color reflectance image and NIR image being well-aligned because both are captured at the same time.

FIG. 3A, more specifically, illustrates an example color filter array 316. As shown by the insert, the color filter array 316 includes an array of four channels 315, 317, 319, 321. The four channels include NIR 315, Red (R) 317, Blue (B) 319, and Green (G) 321. FIG. 3B is a graph 318 showing an example spectral sensitivity for the notch filters which include NIR 315A, R 317A, B 319A, and G 321A. As shown in FIG. 3B, there is crosstalk between the R, G, B, and NIR channels. The color image channels, e.g., R, G and B, are sensitive to the NIR component. The NIR channel may also not be ideal and is sensitive to visible light, an image enhancement technique together with calibration can be used to extract color and NIR imagery from raw images more accurately.

Figures 4A, 4B:
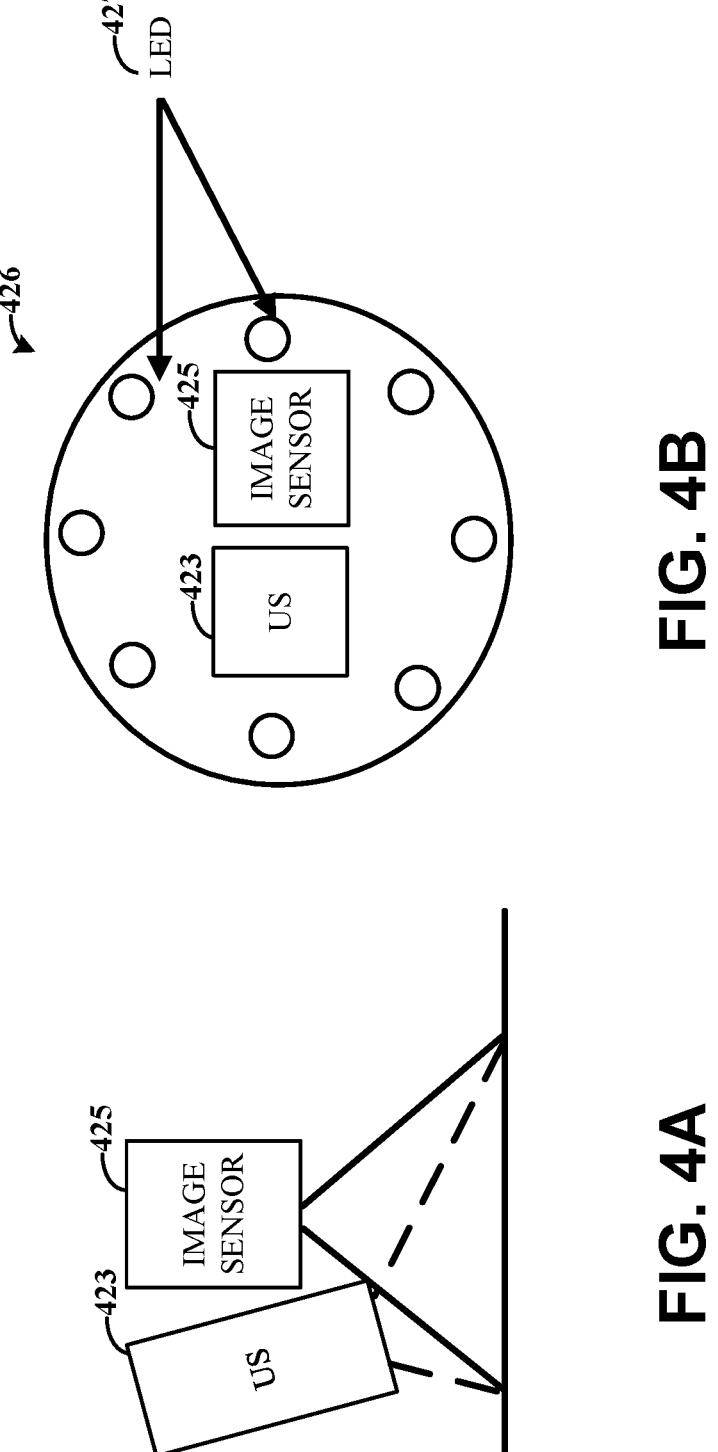
FIGS. 4A-4B illustrate an example of an ultrasonic transducer and image sensor placement, in accordance with various embodiments.

FIGS. 4A-4B illustrates an example of an ultrasonic (US) transducer and image sensor placement, in accordance with various embodiments. Embodiments herein are directed to imaging apparatus that visualize soft tissues using different, yet complementary modalities.

As previously described, the different modalities can include visible polarized light, NIR polarized light, and, optionally, shear wave ultrasound, which have different advantages over the other. NIR has advantages over visible-light range, such as deeper tissue penetration due to less absorption by hemoglobin and water. Also, these soft tissues have special aspect ratios of the tissue cells compared to others in the body. Utilizing polarized NIR can result in a strong anisotropic interaction with light. Ultrasound has much deeper range of the penetration and is able to assess the tissue strain and elasticity of the anatomical structures. Using different ultrasound techniques, such as frequency compounding, and harmonic imaging, can further enhance to differentiate soft tissues from surrounding other structures.

Both polarized NIR and ultrasound imaging are ionizing radiation free and are safe to patients and staff during surgery. With multimodal sensing, the imaging apparatus can fuse and align the fine image features from each modality into a single video stream that can be used to present a single registered view, such as to the surgeon or to a guide robot for navigation.

Soft tissues are often hidden by other anatomical structures and/or located in deeper depths than may be visible by optical imaging. Ultrasonic images can be used and combined to provide additional information. As shown by FIG. 4A, the use of the combination of these modalities relies on the registration of both ultrasound and image (e.g., NIR/VIS) sensors 423, 425 at the probe level, e.g., the ultrasound imaging probe 423 can be placed next to the image sensor 425 and the light sources 427 are distributed at the periphery of the ultrasound transducer shown in FIG. 4B. Simultaneous ultrasound and NIR imaging can be achieved with this combined probe 426.

The image sensor 425 can have a plurality of channels (e.g., NIR, red, green, and blue). In a number of embodiments, at a particular time, only the NIR channel of the plurality of channels is activated and/or enabled to register information with the US as NIR has a shallow depth penetration and can overlap the region with US image for registration. In various embodiments, as the NIR and color channels (red, green, and blue) belong to the same sensor, the image sensor 425 can automatically cause the color image to register.

Since images acquired from ultrasound can be generally in shades of grey, soft tissues such as nerves and blood vessels are hyperechoic and appear to be much brighter in the image. These hyperechoic signals can be further enhanced with harmonic imaging and frequency compounding. In addition, ultrasound elastography used to assess the tissue strain and elasticity of the anatomical structures can also be combined with hyperechoic analysis to distinguish soft tissues from surrounding structures, which can make the tissue detection more robust. With all unique tissue characteristics, the imaging apparatus can apply pattern-selective image fusion in conjunction with a contrast normalization algorithm for both ultrasound and NIR images to effectively highlight local image features in a scene that can maximize detection of soft tissues on and/or below the surface.

Figure 5:
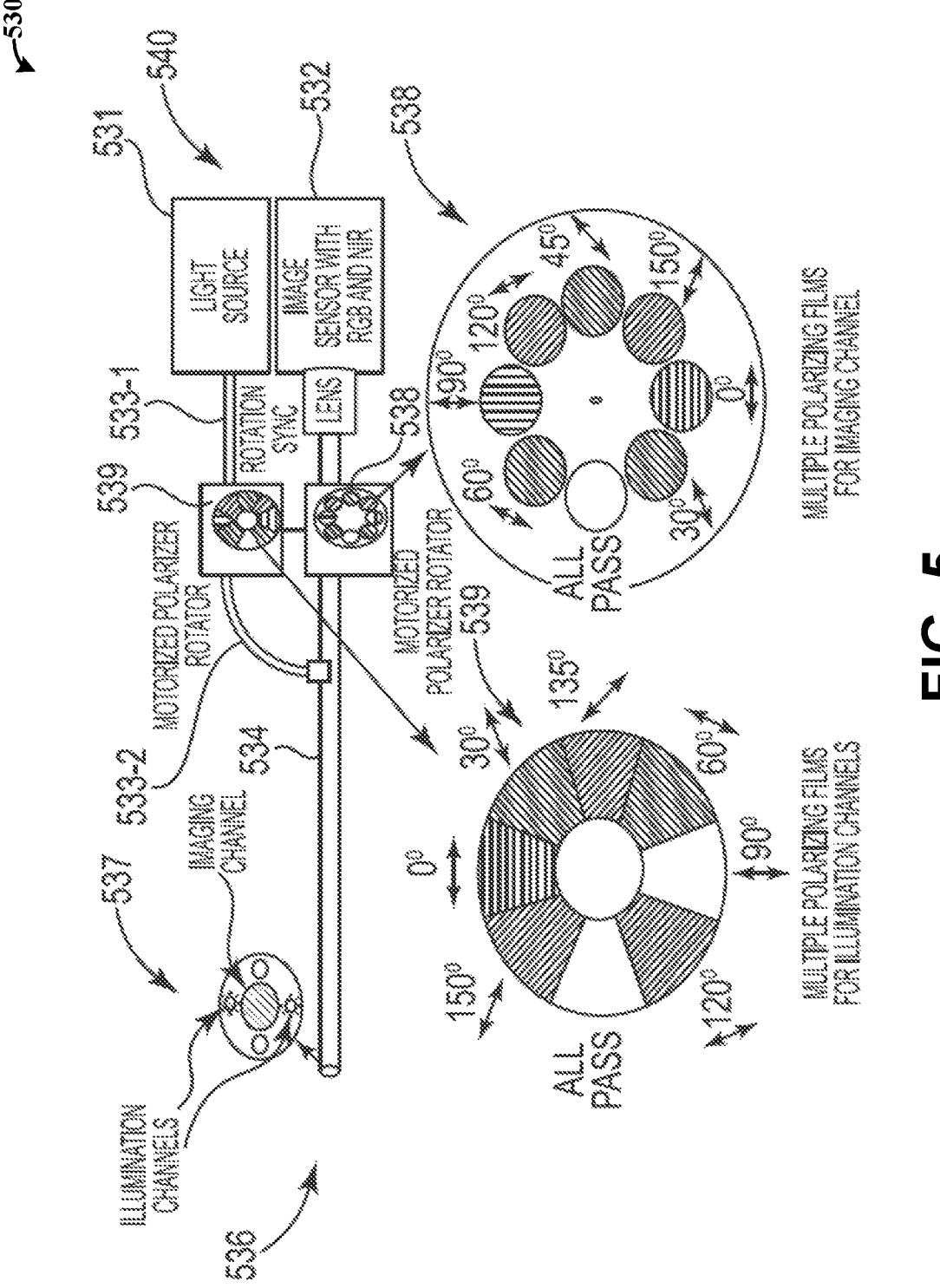
FIG. 5 illustrates an example endoscope, in accordance with various embodiments.

FIG. 5 illustrates an example endoscope, in accordance with various embodiments. As previously described, the image device can form part of an endoscope. The endoscope includes an imaging unit and a light source with a rigid shaft or tube. The shaft is connected to the light source via an "umbilical cord", through which pass other tubes transmitting air, water and suction, etc. Based on the above imaging concept, the polarimetric endoscope can be designed by including, for example, two motorized polarizer rotators in the front of the light source and the camera lens, respectively. This allows for use of the polarized light to image the tissue with backscattered reflection through the nearly polarization maintaining rigid endoscope to the image sensor.

The endoscope 530 has a distal end 540, a proximal end 536, and a rigid tube 534 arranged between the distal end 540 and the proximal end 536. An image sensor 532 is coupled to the distal end 540, and the distal end 540 is arranged with the rigid tube 534 (e.g., a shaft) to provide light reflected from the sample to the image sensor 532. A light source 531 is coupled to the rigid tube 534 via another tube 533-1, 533-2 (e.g., the "umbilical cord") between the distal end 540 and the proximal end 536 and to provide the light beam along the optical pathway.

A first polarizer 539 is positioned proximal to the light source 531. The first polarizer 539 includes a filter that is sized according to illumination channels associated with the other tube 533-1, 533-2 and the light source 531. A second polarizer 538 is positioned proximal to the image sensor 532 along the rigid tube 534. The second polarizer 538 includes a filter that is sized according to an imaging channel associated with the rigid tube 534 and the image sensor 532. The filters can include polarizer rotators 538, 539.

The proximal end 536 can be coupled to an elongated flexible tube, which is configured to be inserted into soft tissue and for imaging the soft tissue. The distal end 540 can include a filter (as illustrated by the illumination channels and light channels 537) used to selectively pass NIR light or wavelengths and visible light or wavelengths.

The two polarizer rotators 538, 539 can include a plurality of polarizers, such as seven linear polarizing films placed at different angles as examples shown in FIG. 5. The number of polarizing films on the wheels/rotators can be increased for finer resolution of angle depending on the application. The shapes of the polarizing films are designed to match with the sizes of imaging channel and illumination channels, respectively. The polarizer rotators 538, 539 are used to synchronize the rotation to form a cross polarization that is an orthogonal angle. For example, the 90 degree of the second polarizer associated with the second polarizer rotator 538 at the lens side is corresponding to the 0 degree of first polarizer associated with the first polarizer rotator 539 at the light source side, while the 120 degree of second polarizer associated with the second polarizer rotator 538 at the lens side is corresponding to the 30 degree of the first polarizer associated with the first polarizer rotator 539 at the light source side, and so on. Among them, one slot of the rotators 538, 539 is used for an all-pass filter, which allows the imaging apparatus to turn off the polarization effect to obtain non-polarized images as the conventional endoscope. The implementation can be also extended for a slant polarization at any arbitrary angle, such as 45 degree slant-polarized, depending on the design pattern of polarizing films. The image sensor 532 can be triggered for image acquisition each time when the polarizer rotators are spun at different cross polarization angles. Multiple polarized images, including visible and NIR channels, for a scene can be acquired and reconstructed by a series of image processing functions including contrast enhancement, image registration, tissue detection and fusion modules to form a single enhanced image.

Figure 6:
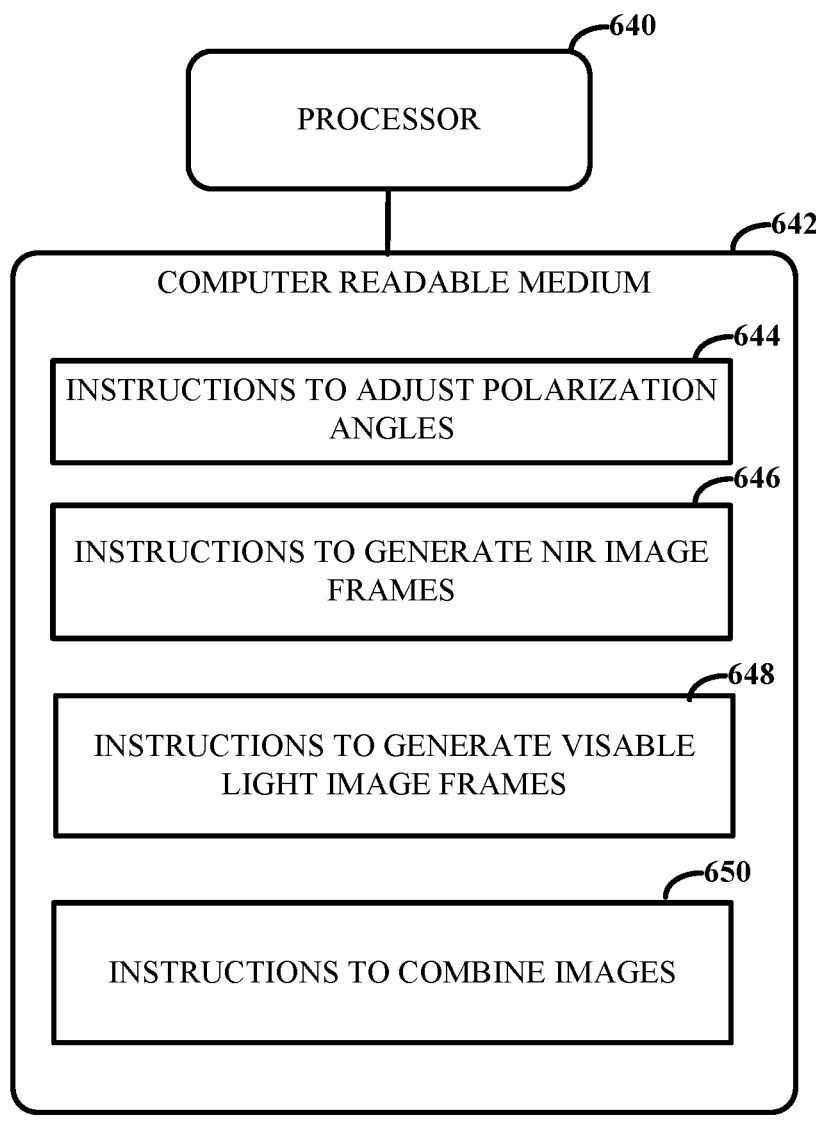
FIG. 6 illustrates an example computing device including non-transitory computer-readable medium storing executable code, in accordance with various embodiments.

FIG. 6 illustrates an example computing device including non-transitory computer-readable medium storing executable code, in accordance with various embodiments. The computing device, in accordance with embodiments herein, includes the image device including the controller, such as illustrated by FIGS. 1 and 2A.

The computing device has processing circuitry, such as the illustrated processor 640, and computer readable medium 642 storing a set of instructions 644, 646, 648, 650. The computer readable medium 642 can, for example, include read-only memory (ROM), random-access memory (RAM), electrically erasable programmable read-only memory (EEPROM), Flash memory, a solid state drive, and/or discrete data register sets. The computing device illustrated by FIG. 6 can form part of the imaging device having the image sensor, such as the processor 640 including part of the control circuitry illustrated by FIG. 1.

The computing device can be used to capture image data of a sample, the image data including and/or being indicative of a plurality of polarized NIR image frames and a plurality of polarized visible light image frames of the sample collected using a plurality of different polarization angles of illumination light and imaging light. For example, at 644, the computing device adjusts the first polarizer and second polarizer to a first polarization angle and a second polarization angle, where the first and second polarization angles are crossed with each other (e.g., orthogonal or slant). The adjustment can include causing or controlling a motor to physically rotate or otherwise change the angle of each polarizer or causing different electrical fields to be applied to the respective polarizers. At 646, the computing device generates an NIR image frame of the sample, and at 648, generates a visible light image frame of the sample while the polarizers are at the first and second polarization angles. In some embodiments, the image sensor includes a color filter array used to capture the NIR image frame and the visible light image frame at the same time. In other embodiments, in order to generate an NIR image frame, the computing device can cause or control a filter to selectively pass the NIR light.

To generate the visible light image frame, the computing device can cause or control the filter (or another filter) to selectively pass the visible light. At 650, the computing device combines the visible and NIR image frames. At 646, the computing device further adjusts the first polarizer and second polarizer to a third polarization angle and a fourth polarization angle, where the third and fourth polarization angles are crossed with each other, and are different than the first and second angles. The computing device can similarly generate an NIR image frame of the sample and generate a visible light image frame of the sample while the polarizers are at the third and fourth polarization angles, at 646 and 648. The computing device can repeat the adjustment of the polarization angles until a plurality of NIR image frames and visible light image frames are captured at a set of a different polarization angles. As previously described, various embodiments are directed to use of different numbers of polarization angles in the set, such as a range of two angles to two hundred angles or more. The number of polarization angles used can be based on the specific application. Additionally, the design of the number angles is empirical. As a specific example, twelve different polarization angles are used with varied intervals, such as angles of −10, 0, 10, 35, 45, 55, 80, 90, 100, 125, 135, and 140 degrees. As another example, seven different polarization angles are used with varied intervals, such as angles of 0, 30, 60, 45, 90, 120, and 150 degrees. However, embodiments are not so limited and different numbers of polarization angles and different varied intervals (e.g., degrees and spacing between respective angles) can be used by the imaging apparatus.

Embodiments are not limited to the above described capturing of the image data. In some embodiments, the computing device can capture the plurality of NIR image frames followed by the visible light image frames. In such embodiments, the image sensor can include one or more filters for selectively filtering the visible light and the NIR light. For example, the computing device adjusts the first polarizer and second polarizer to a first polarization angle and a second polarization angle, where the first and second polarization angles are cross with each other (e.g., orthogonal or slant). The computing device causes the filter to selectively pass the NIR light and to generate a NIR image frame. The computing device repeats the adjustment of the polarizers and captures the plurality of NIR image frames using each of the different polarization angles of the set. Once the plurality of NIR image frames are captured, the computing device adjusts the first polarizer and second polarizer to the first polarization angle and the second polarization angle, and causes the filter to selectively pass the visible light and to generate a visible light image frame. The computing device repeats the adjustment of the polarizers and captures the plurality of visible image frames using each of the different polarization angles of the set.

In various experimental embodiments, imaging of soft tissue can be performed using the two polarizers that are cross each other and using a notch filter (without polarization, such as 410-690 nm and 715-1100 nm). For the polarized images, multiple visible or NIR images can be acquired by rotating (or otherwise causing the adjustment to) both polarizers at the same time with different angles. Based on tissue characteristics of birefringence reflection, polarization imaging can filter out other anatomic structures and result in the best response for nervous-tissue signals. This phenomenon is consistent for all the different wavelengths.

Figure 7B:
FIGS. 7A-7B illustrate example images of visible illumination of nerves without polarization and with polarization, in accordance with various embodiments.
Figure 7A:
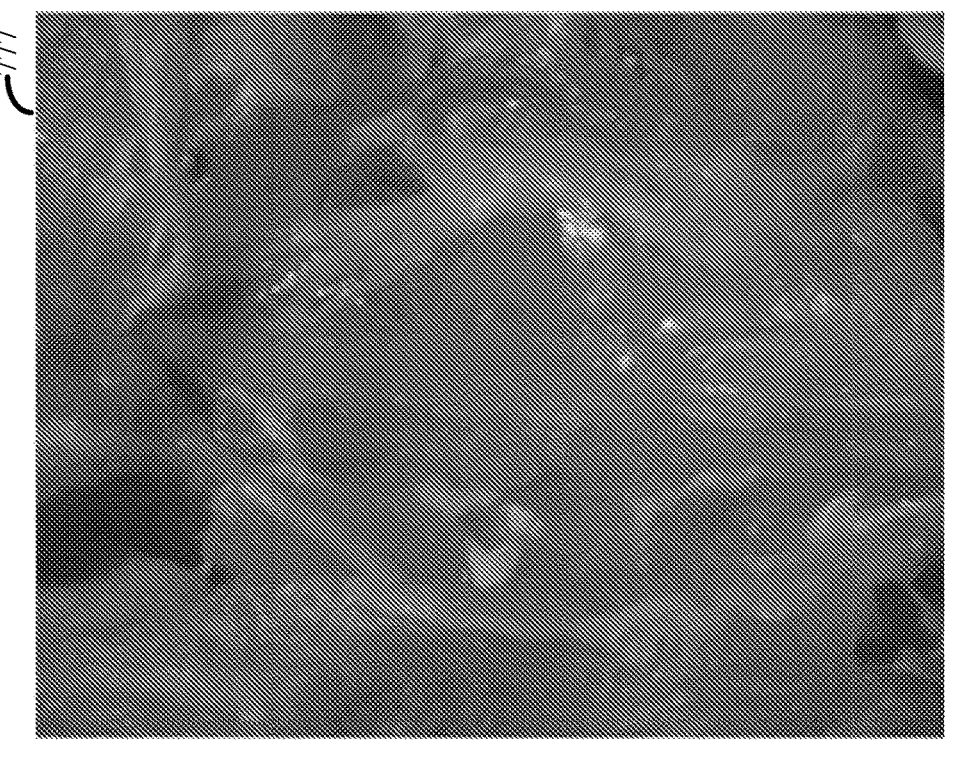

FIGS. 7A-7B illustrate example images of visible illumination of nerves without polarization and with polarization, in accordance with various embodiments. FIG. 7A is an image 777 of rabbit spinal tissue obtained with visible light and using the notch or bandpass filter without polarizations. FIG. 7B is an image 778 of the rabbit spinal tissue obtained with visible light and polarization. As shown by image 777, with the non-polarized visible illumination filtered by a bandpass (410-690 nm) filter, it may not be possible to indicate if and where the nerves originate from the spinal cord. In contrast, as shown by image 778 using the polarization filters and rotating the object 60 degree with respect to polarization direction, the spinal nerve and even small muscular nerve distinctly appear while the other surrounding tissues are smoothed out. The same image sensor can be used to image the object under NIR illumination filtered by a bandpass (715-1100 nm) filter.

Figure 8B:
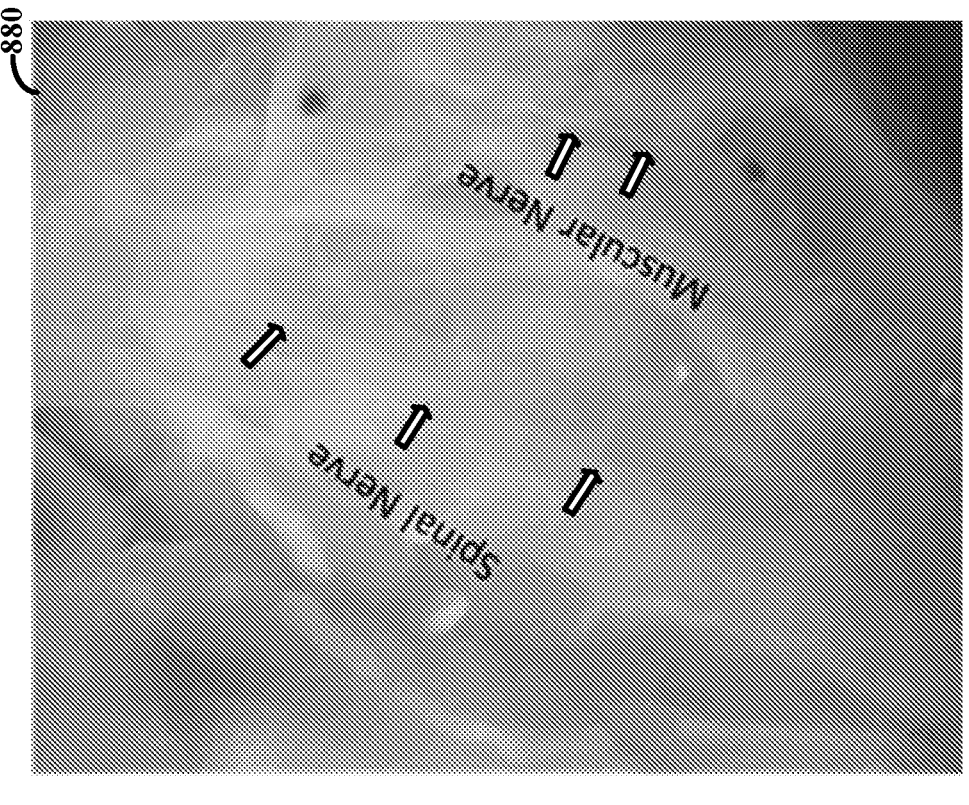
FIGS. 8A-8B illustrate example images of a tissue sample illuminated with NIR light without polarization and with polarization, in accordance with various embodiments.
Figure 8A:
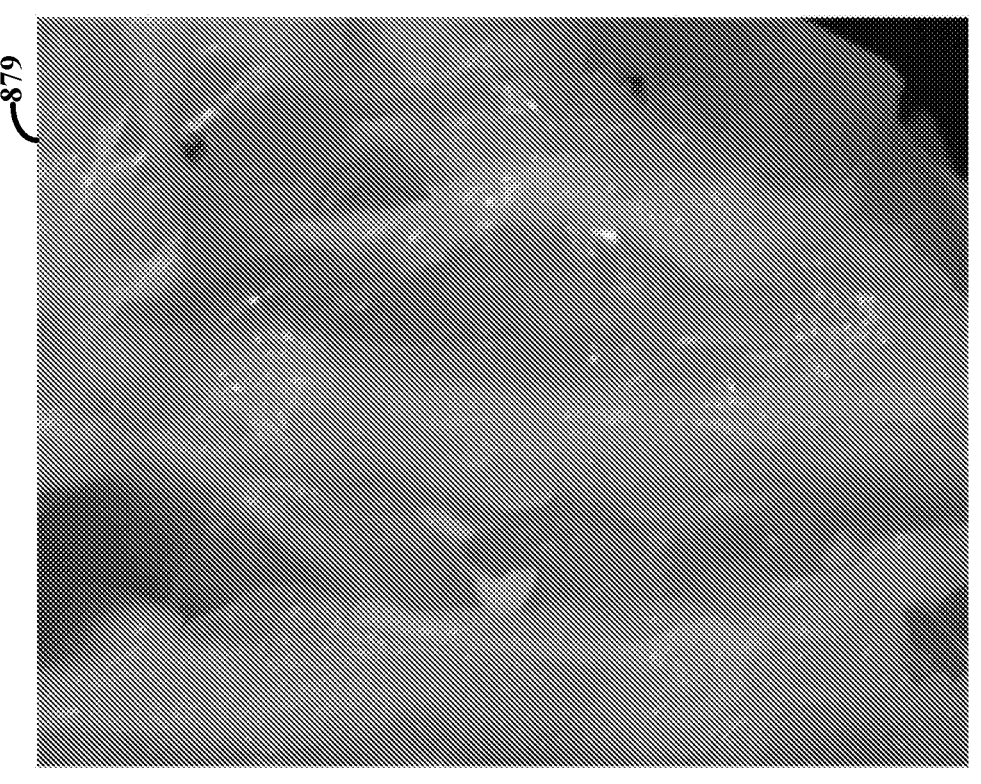

FIGS. 8A-8B illustrate example images of tissue sample illuminated with NIR light without polarization and with polarization, in accordance with various embodiments. FIG. 8A is an image 879 of rabbit spinal tissue obtained with NIR light using the notch or bandpass filter without polarization. FIG. 8B is an image 880 of the rabbit spinal tissue obtained with NIR light and polarization. As with FIGS. 7A-7B, the polarization effect makes the nerve tissues stand out as compared to the non-polarized image 879.

Nerves can be occluded by the blood and other soft tissues during surgery. Another experiment is conducted to compare the light penetration under the occluding conditions. FIGS. 9A-9B and 10A-10B show the imaging results as a red ink over the object surface, simulating the nerve occlusion with blood.

Figure 9B:
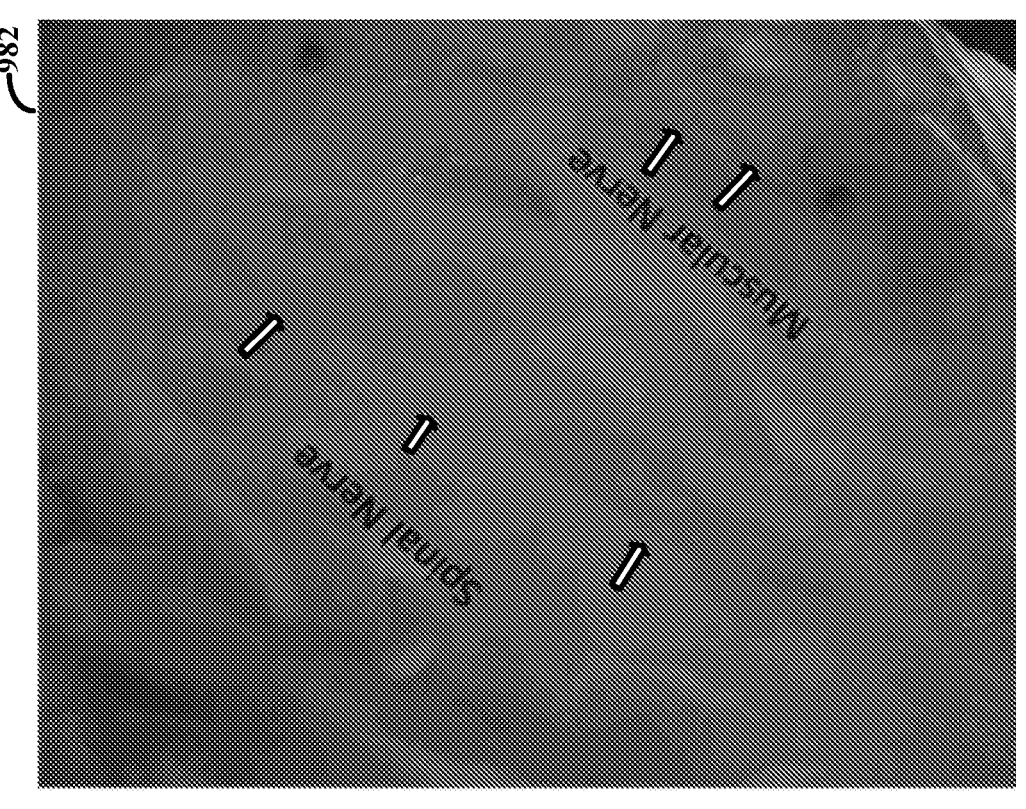
FIGS. 9A-9B illustrate example images of red ink-covered on a tissue surface where visible illumination occurs without polarization and with polarization, in accordance with various embodiments.
Figure 9A:
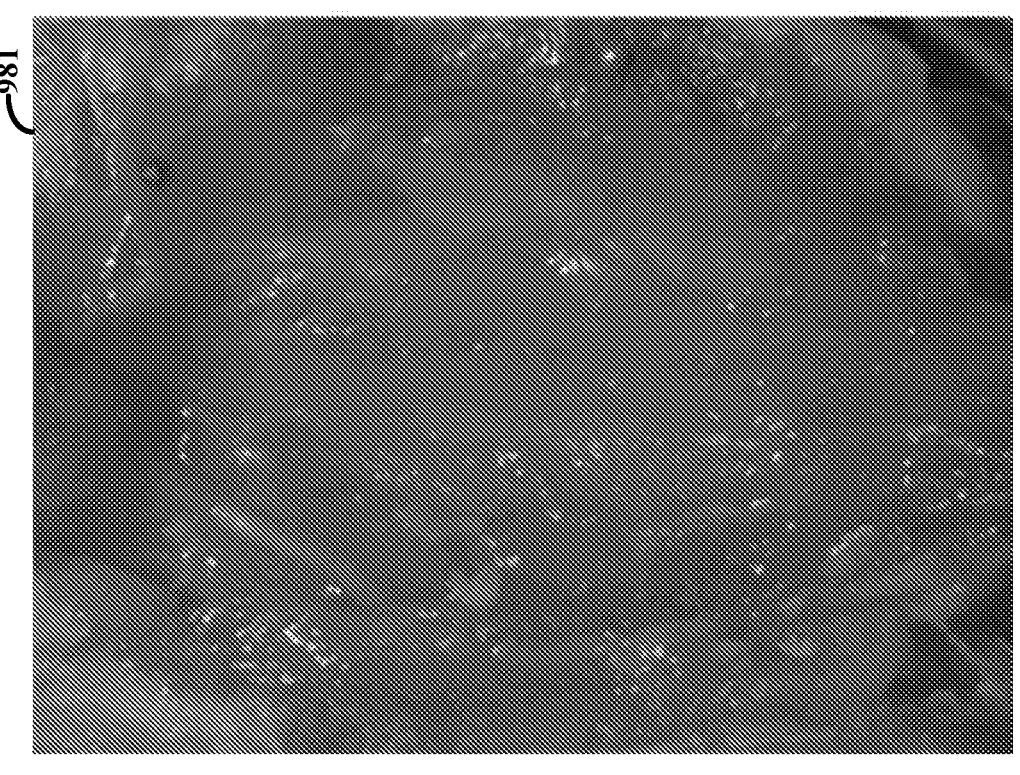

FIGS. 9A-9B illustrate example images of red ink-covered on the tissue surface where visible illumination occurs without polarization, and with cross-polarization, in accordance with various embodiments. For example, FIG. 9A shows an image 981 obtained using visible light and without polarization. FIG. 9B shows an image 982 obtained using visible light and with polarization.

Figure 10B:
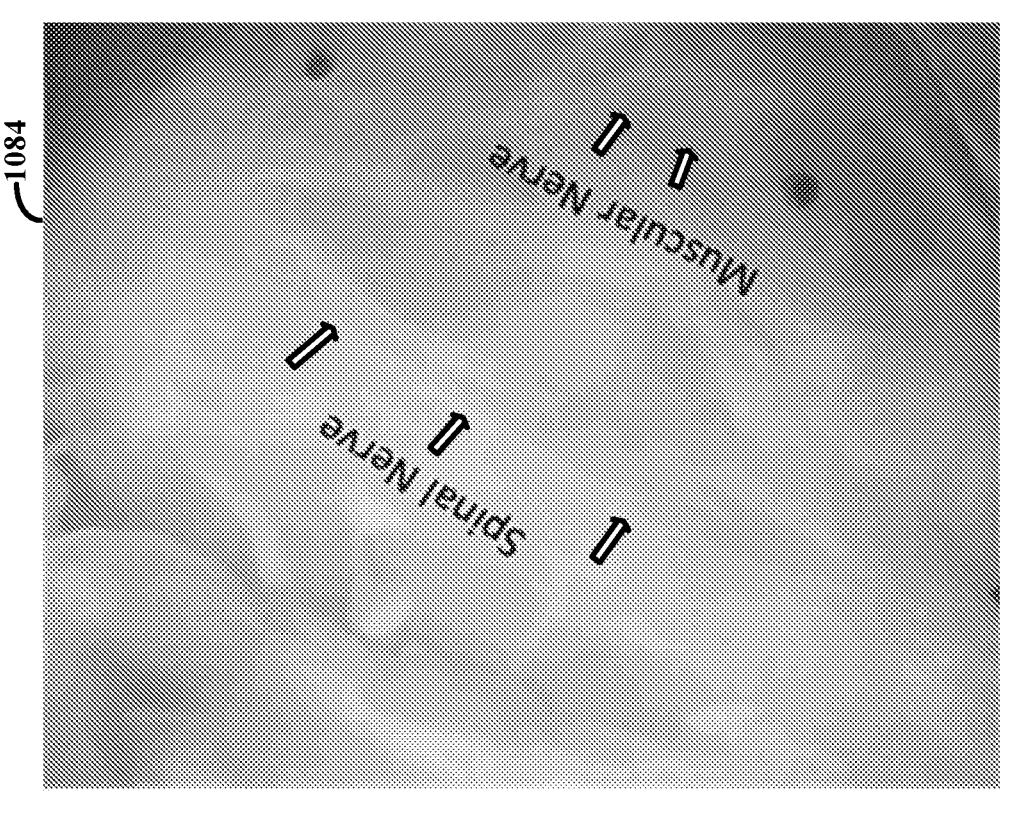
FIGS. 10A-10B illustrate example images of red ink-covered on a tissue surface where NIR illumination occurs without polarization and with polarization, in accordance with various embodiments.
Figure 10A:

FIGS. 10A-10B illustrate example images of red ink-covered on the tissue surface where NIR illumination occurs without polarization and with cross-polarization, in accordance with various embodiments. For example, FIG. 10A shows an image 1083 obtained using NIR light and without polarization. FIG. 10B shows an image 1084 obtained using NIR light and with polarization.

Although all images have the degraded contrast, both visible and NIR imaging with polarization, e.g., images 982, 1083, show better performance than non-polarized imaging, e.g., images 981, 1084. The polarized NIR imaging also shows better depth penetration with less contrast degradation than polarized visible imaging when the red ink is used. It is noted that these shown images are not processed by any image enhancement function. Fusing visible and NIR images with advanced image processing techniques, as further described herein, can even further improve the results.

Figure 11:
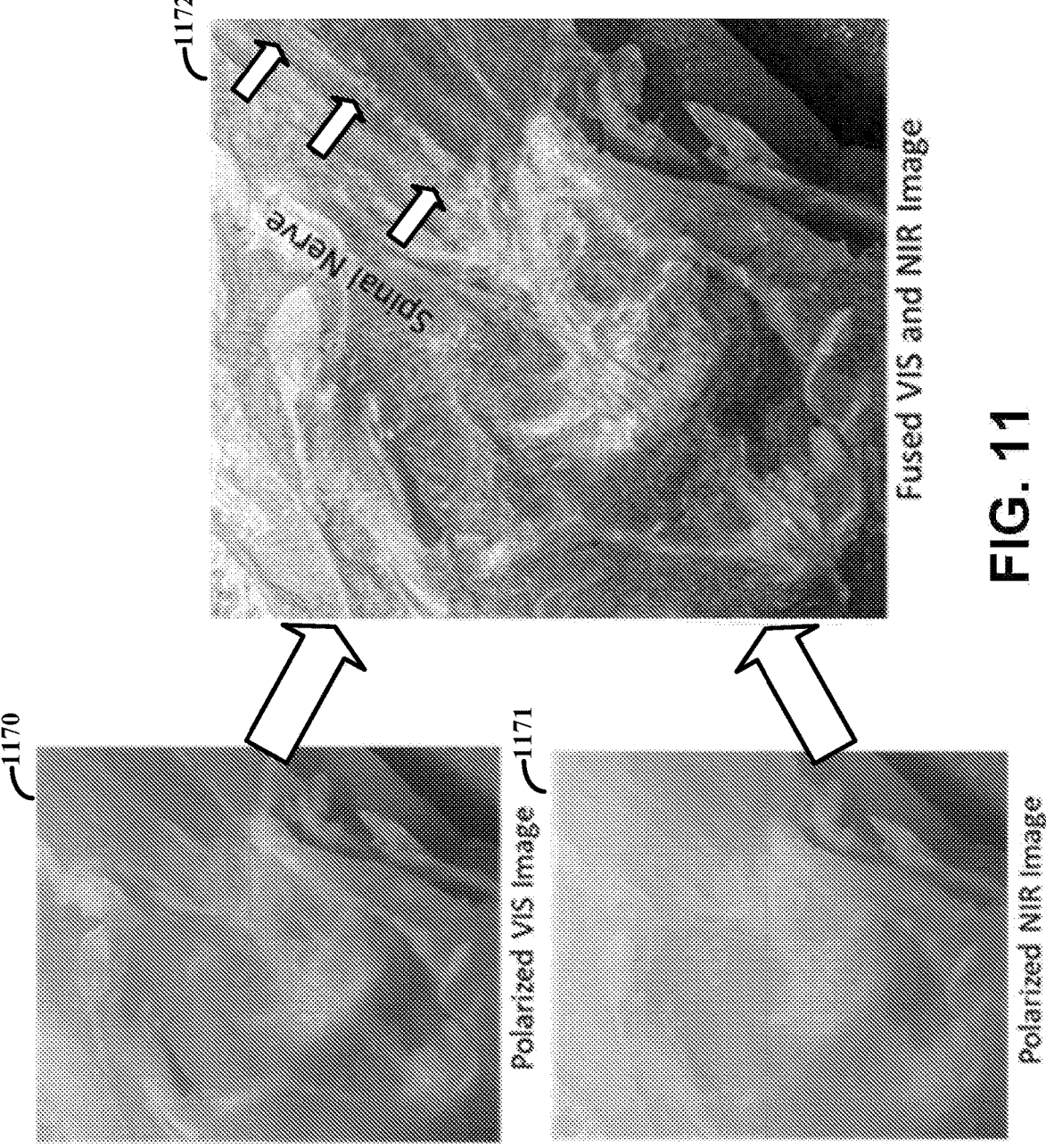
FIG. 11 illustrates example images including a polarized visible light (VIS) image, a polarized NIR image and a fused VIS and NIR image, in accordance with various embodiments.

FIG. 11 illustrates example images including a polarized visible light (VIS) image, a polarized NIR image and a fused VIS and NIR image, in accordance with various embodiments. More specifically, FIG. 11 illustrates a polarized VIS image 1170, a polarized NIR image 1171, and a fused image 1172. The fused image 1172 can produce an optimized view of the soft tissue image for a scene and/or sample. This common surgical view can have a perfect alignment and fusion of the fine image features from two modalities with a single video stream for surgeons.

Figure 12:
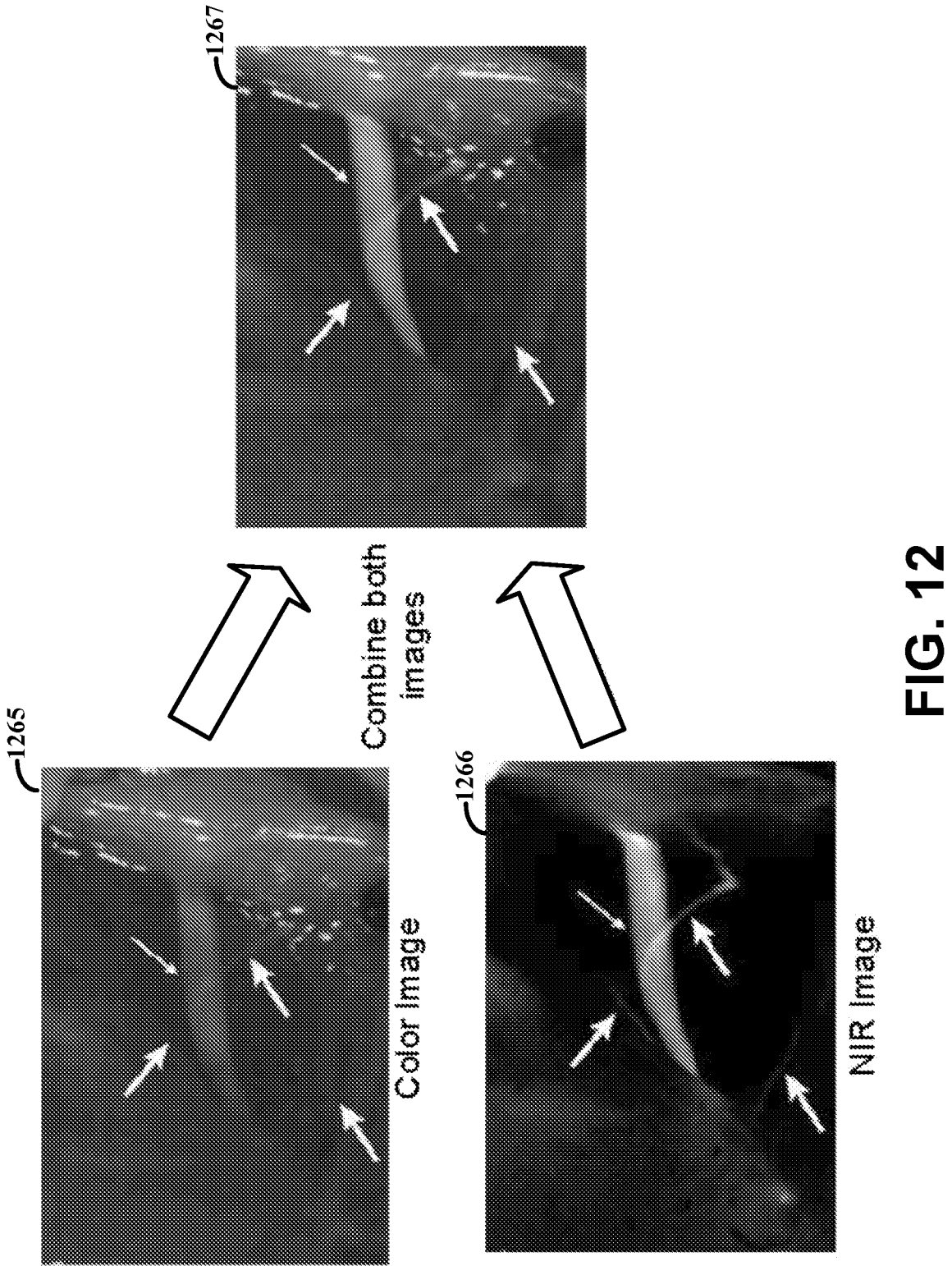
FIG. 12 illustrates an example output of an apparatus, in accordance with various embodiments.

FIG. 12 illustrates an example output of an imaging apparatus, in accordance with various embodiments. More specifically, the imaging apparatus can provide a fused image 1267 from a visible light image 1265 and a NIR image 1266 that includes a simultaneous display of both images with time-multiplexed illumination and detection. The fused image 1267 can resemble a fluorescent technique, and allow for alignment and fusion of features from the two modalities in a single view. In specific embodiments, the image data is provided as a single video stream, in real time. The combined inputs can include visible light image frames, NIR image frames, and/or ultrasonic information. In some embodiments, the MR images can be combined with US for processing and the output corresponds to regions between the NIR and US for visualization. In various embodiments, additional inputs can be used, such as electrocardiogram (ECG)/electromyography (EMG), motor evoked potentials (MEP), somatosensory evoked potential (SSEP) and/or other physiological inputs (e.g., vibration, temperature, pressure) which can be used for neuromonitoring. A pattern can be observed from these signals, such as in time or frequency domain, which can be learned over time and used to monitor nerve health condition.

Figure 13:
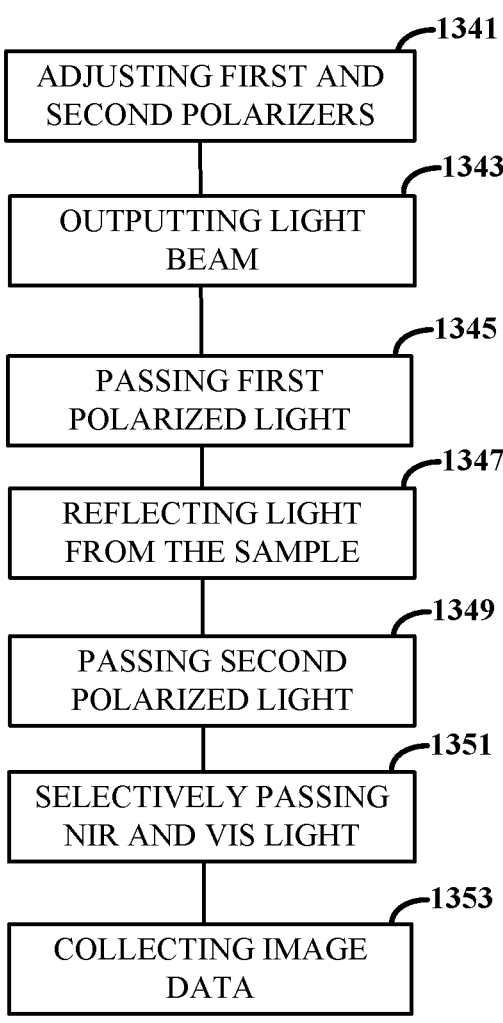
FIG. 13 illustrates an example method for providing images using an apparatus, in accordance with various embodiments.

FIG. 13 illustrates an example method for providing image data using an apparatus, in accordance with various embodiments. The method can be implemented using an imaging apparatus, such as that illustrated by FIGS. 1 and 2A.

At 1341, the method includes adjusting a first polarizer and a second polarizer to different polarization angles with respect to one another, wherein the first and second polarizers are linear and cross each other and while at each of the different polarization angles. At 1343, the method includes outputting a light beam along an optical pathway using a light source. At 1345, the method includes passing, using the first polarizer, first polarized light from the output light beam and toward a sample along the optical pathway, at 1347, reflecting light from the sample responsive to the first polarized light, at 1349, passing second polarized light, using the second polarizer, from the reflected light and toward an image sensor, and at 1351, selectively passing the second polarized light in a visible light range and a NIR light range toward the image sensor. Adjusting or shifting the first and second polarizers to the different polarization angles results in optical reflections of birefringence from portions of the sample to be focused or discriminated when aligned to polarization of collimated incident light, and the method further including identifying which of the different polarization angles of the first and second polarizers results in an area of interest of the sample being in focus.

The method further includes, at 1353, collecting, using the image sensor, image data of the sample from the reflected light while the first and second polarizers are at the different polarization angles with respect to one another and while the visible light and the NIR light ranges (or wavelengths) of the second polarized light are selectively passed. Collecting the image data can include causing a filter to selectively pass the visible light range and the NIR light range, and collecting a plurality of image frames of the sample while the first and second polarizers are at the different polarization angles with respect to one another, while the filter selectively passes the visible light or wavelengths, and while the filter selectively passes the NIR light or wavelengths. In some specific embodiments, collecting the image data includes collecting a sequential order of image frames responsive to the first and second polarizers being at the different polarization angles with respect to one another, and while a filter selectively passes both the NIR and visible light ranges. In other specific embodiments and/or in addition, collecting the image data includes capturing first image data using collimated incident light as generated by the first and second polarizer and capturing second image data using non-polarized light from the light source. The captured first and second image data can include still images and/or video of the sample.

The method can further include generating an NIR image and a visible image from the image data collected while the first and second polarizers are at the different polarization angles and fusing the NIR image and visible image into a single image. For example, the image data includes a plurality of NIR image frames and a plurality of visible light image frames captured while the first and second polarizers are at each of the different polarization angles, and the method further including fusing together the plurality of NIR image frames and the plurality of visible light image frames into a single optimized image.

As described above, the image data captured by the imaging apparatus can be processed using a variety of functions to enhance and detect the important objects, such as soft tissues for image guided surgery. Such image enhancing, as described below, is not limited to images captured using the above-described imaging apparatus and/or for soft tissues. For example, another imaging apparatus can include a plurality of imaging sensors used to respectively capture NIR and visible light images. Each imaging sensor can be associated with a different polarizer that provides different polarization angles. Additionally, the images may not be of soft tissues, such as for use in three-dimensional imaging or printing and/or for in-field images of particular objects and/or portions of the objects. Embodiments are directed to a variety of different imaging apparatus that can capture multiple VIS images and NIR images with polarization at different angles, and the processing circuitry obtains that same and processes the images to fuse into a single image with an area of interest highlighted. In specific embodiments, the area of interest includes the soft tissues, although embodiments are not so limited.

Figure 14:
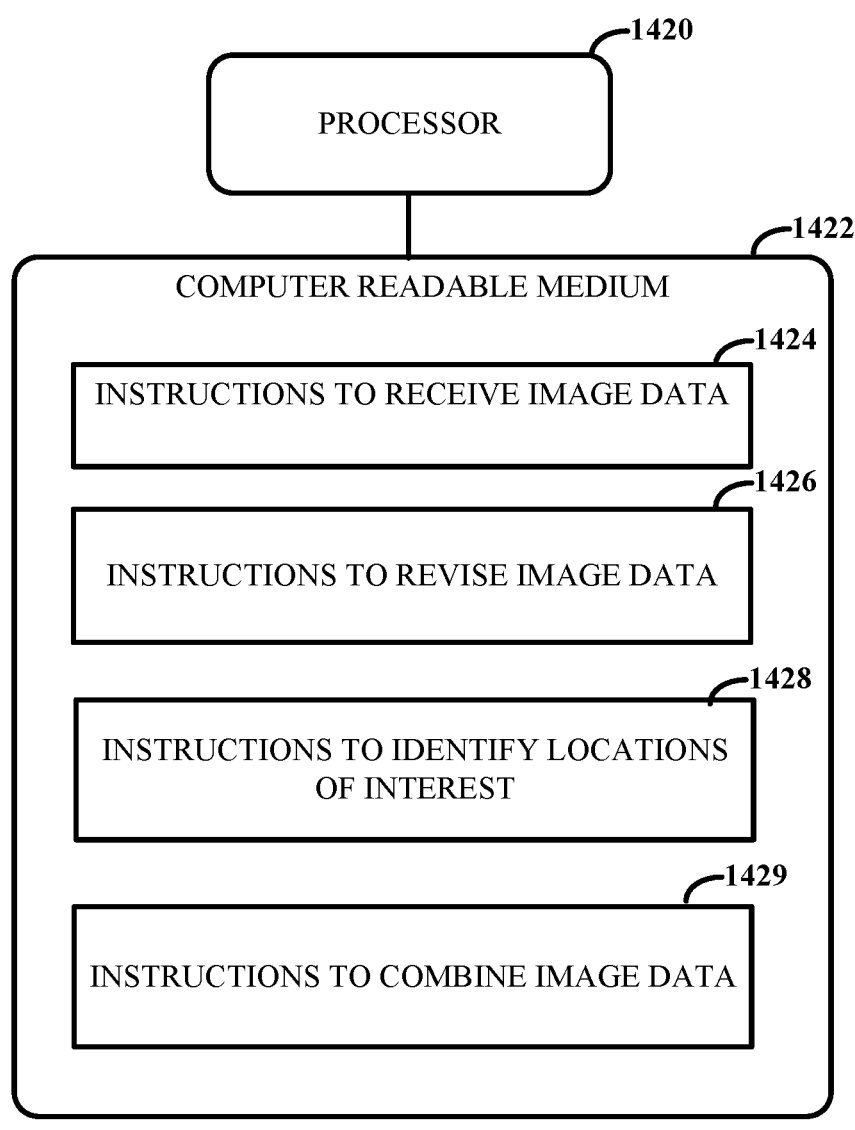
FIG. 14 illustrates an example computing device including non-transitory computer-readable medium storing executable code, in accordance with various embodiments.

FIG. 14 illustrates an example computing device including non-transitory computer-readable medium storing executable code, in accordance with various embodiments. The computing device, in accordance with embodiments herein, includes a computer device having a processing circuitry, such as illustrated by FIG. 1. For example, the processing circuitry can be separate from the imaging device and/or in communication with the image device via control circuitry.

The computing device has processing circuitry, such as the illustrated processor 1420, and computer readable medium 1422 storing a set of instructions 1424, 1426, 1428, 1429. The computer readable medium 1422 can, for example, include ROM, RAM, EEPROM, Flash memory, a solid state drive, and/or discrete data register sets. At 1424, the computing device can receive image data of a sample, the image data including a plurality of polarized NIR image frames and a plurality of polarized VIS image frames of the sample collected using a plurality of different polarization angles of illumination light and imaging light. The illumination light and the imaging light can include a plurality of first polarized light and a plurality of second polarized light that are crossed with each other and for the plurality of different polarization angles, as described above.

At 1426, the computing device revises the image data to improve an image contrast of areas of interest (e.g., soft tissues) in the image data of the sample. The image data can be revised, for example, by adjusting a contrast of the image data and, thereby, increasing salient features of the sample. As further illustrated by FIG. 16, the adjustment to the contrast can be achieved and/or include image enhancement using Contrast Limited Adaptive Histogram Equalization (CLAHE) and bilateral filters, image alignment using Oriented FAST (Features from Accelerated Segments Test) and Rotated BRIEF (Binary Robust Independent Elementary Features) (ORB) and shape matching, and image fusion.

In specific embodiments, the polarized VIS image frames have a contrast adjusted by converting red, green, and blue channels of the plurality of polarized visible light image frames to Y, Cb, and Cr color spaces and computing a plurality of histograms, each histogram corresponding to the Y color space of a section of the plurality of polarized visible light image frames. The converting and computing of histograms can include use of CLAHE filtering which divides images into tiles of width and height pixels. Based on the plurality of histograms, light intensity values in the plurality of polarized visible light image frames are redistributed and a bilateral filter is applied to the Y color space of the plurality of polarized VIS image frames. The redistributed light intensity values are combined with the bilateral filtered Y color space based on local energy of the respective section, and the combined Y color space, along with unchanged versions of the Cb and Cr color space which are all converted to the red, green, and blue channels.

In related and specific embodiments, the polarized NIR image frames have a contrast adjusted by computing a plurality of histograms, each histogram corresponding to light intensity values in a section of the plurality of polarized NIR image frames (e.g., CLAHE filtering which divides image into tiles of width and height pixels). Based on the plurality of histograms, the light intensity values in the plurality of polarized NIR image frames are redistributed, a bilateral filter is applied to the light intensity values of the plurality of polarized NIR image frames, and the redistributed light intensity values are combined with the bilateral filtered light intensity values based on local energy of the respective section.

Improving the contrast can further include image alignment. The following is a specific example of image alignment of two image frames of the plurality of polarized NIR image frames and the plurality of polarized VIS image frames, which can include an image alignment process. Keypoints are identified in each of the two image frames, such as by using a FAST keypoint detector and BRIEF descriptor, or other types of descriptors such as a SIFT/SURF descriptor. The shape descriptors of features of the sample are identified by dividing boundaries of shapes (e.g., divide into smaller and smaller parts). The shape descriptors are used to sort keypoints between the two image frames based on a measure of similarity to the boundaries. A homography is estimated using the sorted keypoints to match keypoints between the two image frames, and the homography is used to align (e.g., map) pixels in the two image frames and output the aligned image frames.

Improving the contrast can further include image fusion. A specific example of image fusion includes generating a pyramid transform for the each of the plurality of polarized NIR image frames and the plurality of polarized VIS frames. For example, a gradient-of-Gaussian patterns for each pyramid level at different scales can be provided. Using each pyramid transform, a match measure is determined based on local normalized correlation at each sample position (e.g., used to determine the mode of combination), and salience measures based on local region energy (e.g., used to determine which image pattern to select in the selection process). A composite pyramid is generated from the pyramid transforms by selecting salient component patterns from the pyramid transforms based on the sample positions in which the salience measures are different, and the composite image is generated through inverse pyramid transform based on the composite pyramid.

At 1428, the computing device identifies locations of the areas of interest in the image data. The locations are identified by aligning the image data, including aligning the plurality of polarized NIR image frames with the plurality of polarized VIS image frames. As further illustrated by FIG. 16, the identification of the locations of the areas of interest Can be achieved and/or include, image preprocessing using a Common Objects in Context (COCO) dataset, object detection using Fast Region-Convolution Neural Network (R-CNN), and/or object segmentation using Mask R-CNN. Although the below embodiments describe use of a COCO data set, Fast R-CNN, and/or Mask r-CNN, embodiments are not so limited. For example, COCO, Scene Understanding (SUN), ImageNet Large Scale Visual Recognition Competition (ILSVRC), Pattern Analysis Statistical Modelling and Computational Learning (PASCAL) Visual Object Classes (VOC) datasets and/or combinations thereof may be used for image preprocessing, such as augmentation and training. As another example, Faster R-CNN, You Only Look Once (YOLO), and/or Single Shot Detector (SSD) may be used for object detection and Mask R-CNN, Deep-Lab, and/or Pyramid Scene Parsing Network (PSPNet) may be used for object segmentation.

Aligning image frame, in specific embodiments, includes image preprocessing, object detection, and object segmentations. Image preprocessing can include use of a training set of annotations in sample images, such as via a training procedure using weighted models and a COCO dataset. The training set can be systematically modifying for a plurality of different conditions (e.g., orientation, location, scale, brightness, etc.), which includes flipping, rotating, scaling, cropping and translation, and Gaussian noise applied to increase the dataset size. The training set can be augmented for soft tissue (e.g., revised surgical scenes with blood occluded soft tissue or haze caused by surgical smoke and transfers based on Generative Adversarial Networks (GANs)) including transforming a training image from one domain to another domain (e.g., grab blood and mix it with another image that has soft tissue exposed).

Object detection can include the use of Faster R-CNN. For example, a feature map having anchors (e.g., region proposals) is generated in the plurality of polarized VIS image frames and the plurality of polarized NIR image frames using different size anchor windows. Each anchor can include a boundary of the respective image frame likely to contain a respective feature (e.g., object or part of the tissue). For each anchor of the feature map, an anchor classification and probability of each anchor containing the respective feature is generated. Anchors are selected based on the probability, and the location and size is refined to fit over the respective feature (e.g., if anchors overlap too much, one with highest foreground score is kept and rest are discarded). Further, each of the anchors of the feature map are resized to a fixed size (e.g., ROI pooling), and used to generate revised anchor classifications (e.g., types of objects or tissue) and a revised probability of each anchor containing the respective feature. Final anchors are identified including the identification of the features having boundaries based on the revised probabilities, the final anchors are output as restored to an original size and location corresponding to the image frame.

Object segmentation can include the use of Mask R-CNN. For example, image masks for the final anchors are generated. The image masks hide portions of the image frames and reveal other portions that include the feature (e.g., set some of the pixel values to zero or a background value). In some specific embodiments, the image masks can be set to soft values, meaning that the pixel intensity is set to a value that depends on how much of an individual pixel is inside the mask.

At 1429, the computing device combines the plurality of polarized NIR image frames and the plurality of polarized visible light image frames into a single composite image of the sample based on the revised image data and the identified locations of the areas of interest. For example, the aligned image frames (from the homography) are used to generate the single composite image that enhances contrast and color channels compared to the plurality of polarized NIR image frames and the plurality of polarized VIS image frames. Combining images can include combining the plurality of polarized VIS frames to form a composite visible image, combining the plurality of polarized NIR image frames to form a combined NIR image, and combining the composite visible image with the composite NIR image to form the single composite image. Each of the composites can be combined using the above provided steps, with the images being combined to provide an optimized view of the sample. The composite can have higher amounts of information than content obtained directly by the image sensor.

In a number of specific embodiments, the processing circuitry can provide feedback to the image sensor used to collect the image data based on the single composite image. The feedback can include data indicative of a subset of the plurality of different polarization angles of the illumination light and imaging light. The subset can, for example, include an optimized set of angles of polarization for the illumination light and the imaging light based on the single composite image and object segmentation.

The processing circuitry cam provide the feedback data to the image sensor used to collect the image data by tracking changes in feature characteristics (e.g., orientation, size, aspect ratio, surface texture, compactness, etc.) using the single composite image and image masks for the final anchors, and comparing energy of the features in the plurality of polarized NIR image frames and the plurality of polarized VIS frames using the single composite image. The energy can be computed from light intensity, such as the sum of the square of the intensity gradient in a small pixel region. Based on the comparison, the processing circuitry selects the most significant image frames from among the plurality of polarized NIR image frames and the plurality of polarized VIS frames which contribute to the energy of the composite image, and outputs the feedback data to the image sensor circuitry that includes an optimized polarization set based on the most significant image frames for guiding the image sensor circuitry for the particular features.

Figure 15:
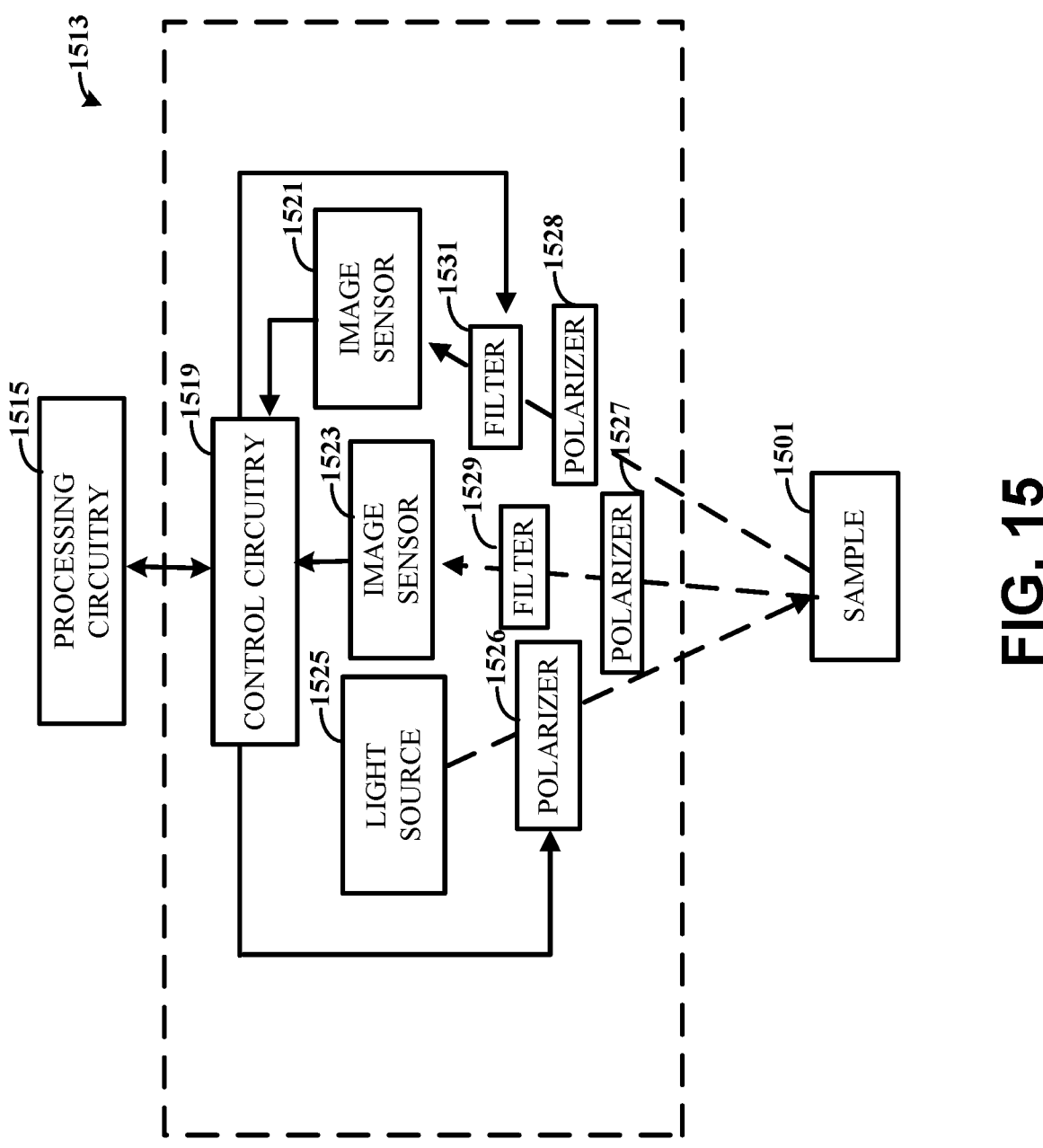
FIG. 15 illustrates another example apparatus, in accordance with various embodiments.

FIG. 15 illustrates another example apparatus, in accordance with various embodiments. As previously described, imaging apparatuses in accordance with the present disclosure are not limited to the imaging apparatus illustrated by FIGS. 1 and 2A, which includes a single image sensor.

The apparatus 1513 includes at least one image sensor 1521, 1523 arranged with control circuitry 1519. The at least one image sensor 1521, 1523 collects image data of a sample 1501 with the image data including a plurality of polarized NIR image frames and a plurality of polarized VIS image frames that are captured using a plurality of different polarization angles of illumination light and imaging light.

The apparatus further includes processing circuitry 1515 that processes the image data captured by the at least one image sensor 1521, 1523. The processing circuitry 1515 can revise the image data to improve an image contrast of areas of interest (e.g., soft tissues) in the image data of the sample 1501, identify locations of the areas of interest in the image data, and combine the plurality of polarized NIR image frames and the plurality of polarized VIS image frames into a single composite image of the sample based on the revised image data and the identified locations of the areas of interest. In various embodiments, as described above, processing circuitry 1515 provides feedback to the control circuitry 1519 based on the single composite image, the feedback being indicative of a subset of the plurality of different polarization angles of the illumination light and imaging light.

In specific embodiments, the imaging apparatus 1513 is consistent with the previously described imaging apparatus of FIG. 1. For example, the imaging apparatus can include a light source 1525 to output a light beam along an optical pathway, first and second polarizers 1526, 1528, and a filter 1531. The first polarizer 1526 is coupled to the light source 1525, and passes first polarized light from the output light beam and toward the sample along the optical pathway. The second polarizer 1528 is arranged along the optical pathway between the sample 1501 and the image sensor 1521, and passes second polarized light from the reflected light and toward the image sensor 1521, wherein the first and second polarizers 1526, 1528 are linear and cross each other. The filter 1531 is arranged along the optical pathway, and passes the reflected light (e.g., the second polarized light) in a visible light range and a NIR light range toward the image sensor 1521. The image sensor 1521 collects light reflected from the sample 1501 in response to passed reflected light. In some embodiments, the control circuitry 1519 causes or controls imaging of the sample 1501 by causing the first polarizer 1526 and the second polarizer 1528 to shift or adjust to the different polarization angles with respect to one another, and by collecting image data of the sample from the reflected light while the first and second polarizers 1526, 1528 are at the different polarization angles with respect to one another and while the filter 1531 selectively passes the visible light and the NIR light ranges of the second polarized light.

However embodiments are not so limited. In various embodiments, one or more of the light source and the image sensor includes a plurality of light sources and/or a plurality of images sensors 1521, 1523 with respective polarizers 1526, 1527, 1528 and filters 1529, 1531. The control circuitry 1519 is arranged with the plurality of image sensors 1521, 1523 to image the sample 1501 by causing the plurality of image sensors 1521, 1523 to capture image data of the sample 1501 using the illumination light and imaging light of the different polarization angles with respect to one another, and by collecting image data of the sample from the plurality of image sensors 1521, 1523.

Figure 16:
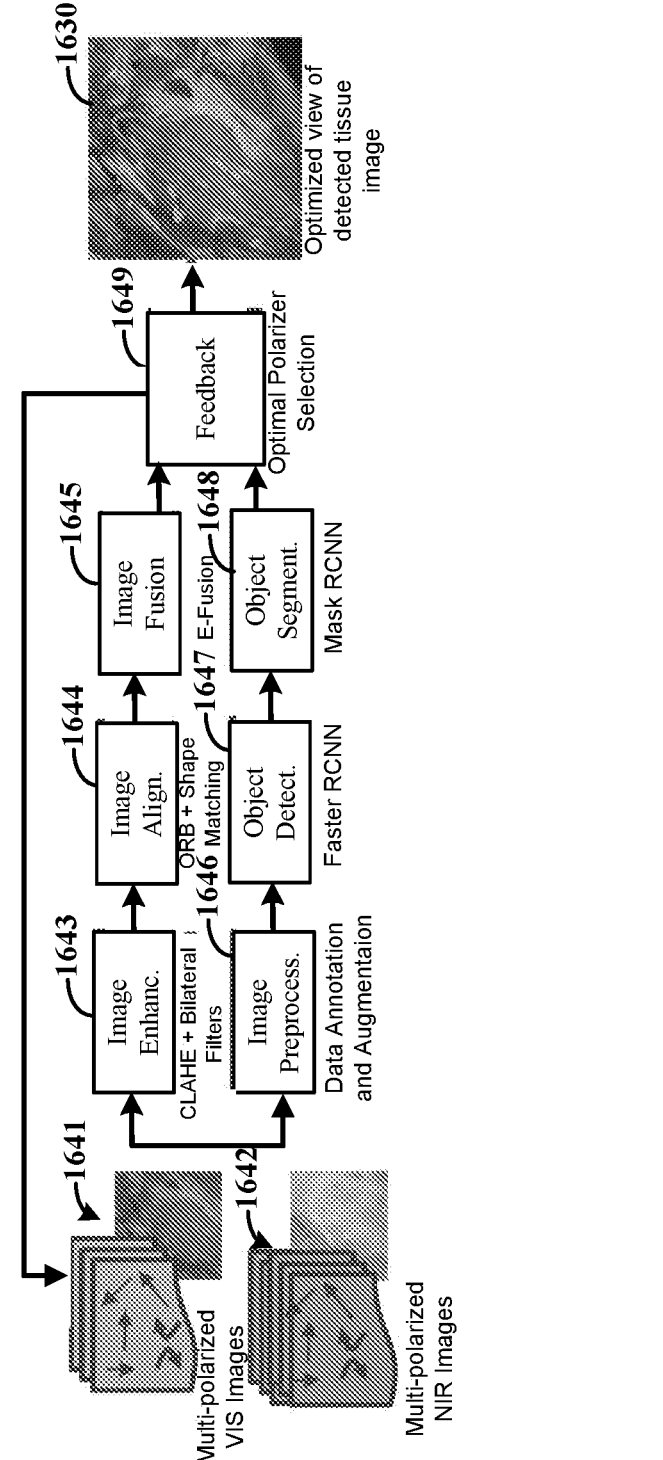
FIG. 16 illustrates an example of various functions used to image processing, in accordance with various embodiments.

FIG. 16 illustrates an example of various functions used to image process image data, in accordance with various embodiments. More specifically illustrated is post-processing 1640 of multiple polarized images 1641, 1642 captured by an image sensor. The plurality of polarized images includes a plurality of polarized VIS image frames 1641 and a plurality of polarized NIR image frames 1642

The post-processing 1640 includes a plurality of modules 1643, 1644, 1645, 1646, 1647, 1648, 1649. Each of the modules 1643, 1644, 1645, 1646, 1647, 1648, 1649 includes computer executable code which can be stored on one or a plurality of non-transitory computer-readable mediums and executed by processing circuitry, such as a single computing device or distribution across multiple computing devices. Furthermore, outputs of the modules can be used as inputs to other respective modules, effectively providing a plurality of feedback loops.

As further described herein, the modules include an image enhancement module 1643, image alignment module 1644, an image fusion module 1645, an image preprocessing module 1646, an object detection module 1647, an object segmentation module 1648, and a feedback control module 1649. Among the modules, the image enhancement, image alignment, and image fusion modules 1643, 1644, 1645 are used to improve the image contrast of soft tissues. The image preprocessing, object detection, and object segmentation modules 1646, 1647, 1648 are used to identify and label the location and region of soft tissues. Although the contrast of soft tissues is improved with polarization imaging, these modules can be used to further enhance the visibility of the soft tissues (or other weak structures) and to produce an optimized view 1630 of the detected tissue image. Each processing module is further described below.

Figure 17:
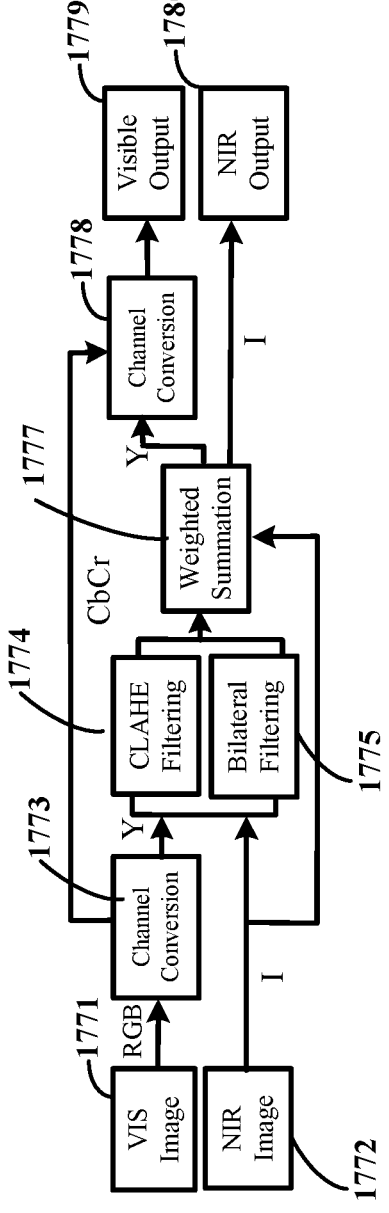
FIG. 17 illustrates an example of an image enhancement module, in accordance with various embodiments.

FIG. 17 illustrates an example of an image enhancement module, in accordance with various embodiments. The aim of image enhancement is to tune the perception of image quality to the perspective of human observers as well as to increase the salient features of soft tissue for the subsequent image analysis. The image enhancement module includes use of a CLAHE filter for both visible images and NIR images. Adaptive histogram equalization (AHE) can be used to improve contrast in images by computing several histograms, each corresponding to a distinct section of the image, and which are used to redistribute lightness values of the images. CLAHE is a type of AHE in which contrast amplification in a vicinity of a given pixel value is provided by a slope of the transform function.

To process the visible images, the RGB channels of a visible image 1771 are converted into the YCbCr color space, at 1773. At 1774, the CLAHE filter is applied to the luminance component Y, while Cb and Cr channels remain unchanged. The drawback of CLAHE is that it works well over homogeneous regions but not over heterogeneous regions where the structures are particularly weak, as most soft tissues appear. The bilateral filter, at 1775, which is a non-linear edge-preserving filter, is applied to prevent or mitigate weak edge signals from being diminished by the CLAHE filter at 1774. At 1777, the result of these two filters can be combined by a weighted summation based on the local energy of the region. The luminance component Y of the visible image is merged with the original Cb and Cr, at 1778, to produce an output enhanced RGB image, at 1779.

The same process is carried out for NIR images 1772. Because NIR images 1772 have no color channels, the NIR images 1772 are processed with intensity (I). Like the visible spectrum images, a CLAHE and a bilateral filter is applied to the image, at 1774 and 1775. The original image is merged with the filtered versions, at 1777, to create an image that is contrast enhanced but with a similar texture level as the original, and with the enhanced image being output at 1780.

A CLAHE filter is used for both the visible and NIR images to improve the contrast of the images by computing several histograms, each corresponding to a section of the image, and by redistributing lightness values of the images. For example, the images can be divided into sections or tiles of a width and height of the pixels, which can be larger than a size of the features to be observed. As visible light include RGB channels, the visible image frames are converted to the YCbCr space, and the CLAHE filter is applied to the Y channel while the CB and Cr channels remain unchanged. Additionally, the bilateral filter is applied to the Y channel to mitigate weak edge signals from being diminished and the results are combined with the original image by a weighted summation. The NIR frames are processed based on I only and by application of the CLAHE filter and the bilateral filter, with the filter images being combined with the original by a weighted summation. The enhanced output image can have a similar texture as the original.

Figure 18A:
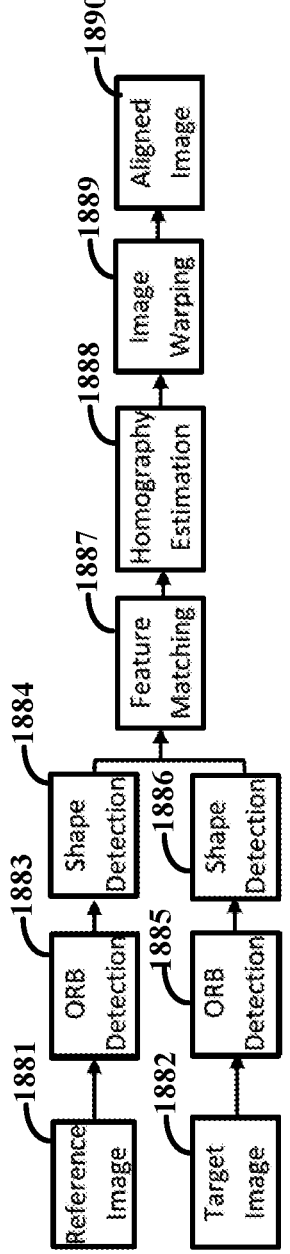
FIGS. 18A-18B illustrate an example of an image alignment module, in accordance with various embodiments.
Figure 18B:
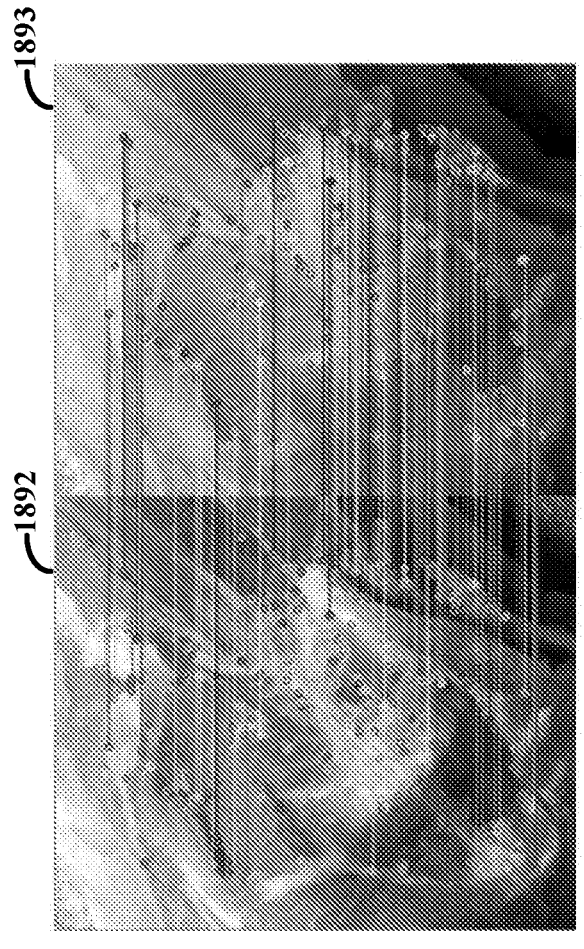

FIGS. 18A-18B illustrate an example of an image alignment module, in accordance with various embodiments. The image alignment module is used to align images when image sensor (e.g., camera) motion is introduced during image acquisition. Although the image sensor illustrated herein is shown as being immobile, image sensor motion can occur when the bandpass filters are switched to acquire multispectral image, among other reasons. This is a design issue that can be avoided, but may be inevitable for practical clinical use where the image sensor is in motion, such as in constant motion. To estimate such a camera motion, it can be assumed that the relationship between two images (e.g., reference image and target image) is a rigid transformation. The image alignment module can be used or be based on ORB approach to match the corresponding points with each other, and which is used to align image frames between one another and combine a plurality of NIR frames into a single NIR frame and a plurality of visible image frames into a single visible image frame.

FIG. 18A shows an example image alignment process using the image alignment module. A reference image 1881 and a target image 1882 are input to the module. At 1883 and 1885, ORB detection identifies so-called keypoints that are produced by a fusion of the FAST keypoint detector and BRIEF descriptor to extract the invariant features under rigid transformation of the reference image 1881 and the target image 1882. More specifically, FAST can be used to identify the keypoints and BRIEF can be used to create feature vectors. Visible images can contain more prominent surface contrast than NIR images that can cause detected keypoints to be not distributed well between and the mapping correspondence result can be very inaccurate. At 1884 and 1886, shape detection is used to divide the boundary of object shape into smaller parts to record the number of contour points and establish a shape descriptor for matching, which is used as a remedy, for each of the reference and the target images 1881, 1882. The shape descriptor can be combined with the ORB descriptor to filter out keypoints that cannot be matched by shape context obtained from the two images 1881, 1882. At 1887, feature matching is used to sort keypoints by goodness of match and may only keep a percentage of original matches. The hamming distance is used as a measure of similarity between two sets of feature descriptors. Only keypoints with measures with greater than a specified threshold are allowed to be used for homography estimation.

At 1888, a homography can be computed when four or more corresponding points in two images are available. However, automatic feature matching does not always produce one hundred percent accurate matches because of outliers. The function of homography estimation can use a Random Sample Consensus (RANSAC) technique to iteratively estimates parameters of a transformation matrix from a set of matching data that contains outliers until they are to be accorded no influence on the value of the correct estimate. RANSAC can produce a correct result even in the presence of a large number of bad matches. At 1889, once an accurate homography is calculated, image warping is applied to all pixels in the target image to map the target image to the reference image. The aligned result is output for image fusion in the next stage, at 1890.

FIG. 18B shows examples of matching points between a reference image (visible) 1892 and a target image (NIR) 1893, where the points with lines connecting the points are qualified for good homography estimation, and while the other points are discarded.

Figure 19:
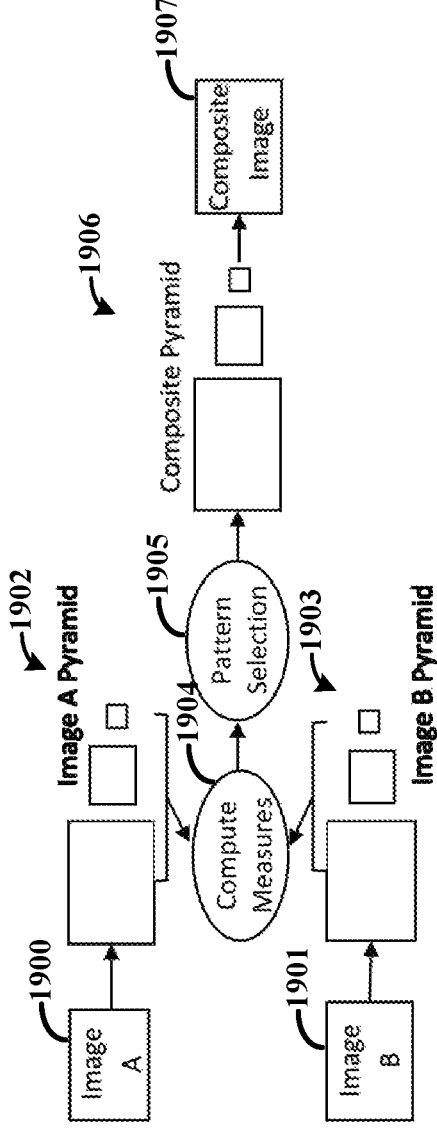
FIG. 19 illustrates an example of an image fusion module, in accordance with various embodiments.

FIG. 19 illustrates an example of an image fusion module, in accordance with various embodiments. Combining near-infrared information with visible images can further enhance the contrast and details and produce more vivid colors. This combination can be achieved using fusion algorithm, based on pyramid transform with a pattern selective approach. FIG. 19 shows the general framework with two source images for simple illustration.

The image fusion process can be carried out in the following steps. At 1902 and 1903, the image fusion module is used to construct a pyramid transform for each source image A 1900 and image B 1901, respectively. The gradient-based pyramid is implemented as the basis functions of the transform that provide gradient-of-Gaussian patterns for each pyramid level at different scales. At 1904, the image fusion module is used to compute two measures: a match measure based on local normalized correlation at each sample position that determines the mode of combination, and salience measures based on local region energy that determine which image pattern can be chosen in the selection process. Guided by these two measures, at 1905, the pattern selection keeps the most salient component pattern from the input pyramids at sample locations where salience measures are distinctly different and copies it to the composite pyramid, while discarding less salient patterns. If salience measures from both images are low or similar, the process averages the pyramid patterns. This way, it reduces noise and provides stability to make the image more natural looking. After two pyramids are combined to form a single pyramid, at 1906, the composite image is recovered through an inverse pyramid transform, at 1907.

In various embodiments, multiple polarized images are obtained with a single image sensor while polarization angles are systematically varied. Two sets of visible images and NIR images with polarization can be fused separately to form a combined visible and NIR image, respectively. The two images are fused again to produce an optimized view of the image. All images can be processed based on this fusion framework to obtain a composite that has greater information content than can be obtained directly from the sensor.

The image preprocessing module cam include or involve an offline process to prepare images for training a deep learning model. For example, a sample of visible and NIR images are selected and annotated by a human expert to label the correct location and region boundary of soft tissues. The annotation results together with the images are saved and divided into a training set and a validation set, respectively.

Rather than using millions of images to train a model from scratch, transfer learning techniques are applied with an existing weights model that is trained based on the COCO dataset. Although the COCO dataset may not contain any soft tissue classes, it contains a lot of other images that the trained weights have already learned regarding the object features common in natural images. The COCO dataset can assist in reducing the number of images used for training.

The image preprocessing module can further include or involve data augmentation to improve the accuracy and robustness of the trained model since the dataset is taken in a limited set of conditions, and the target application can have a variety of conditions, such as different orientation, location, scale, brightness etc. These situations can be accounted for by training the deep learning functions with additional synthetically modified data. Data augmentation techniques including flip, rotation, scale, crop and translation and Gaussian noise are used to increase the size of the available dataset. To further account for surgical scenes that may have blood occluded soft tissues or haze caused by surgical smoke, data augmentation can be further extended with neural style transfers based on GANs, which can transform an image from one domain to an image in another domain. GANs can include a generator neural network that is used to generate new data instances and a discriminator neural network that is used to evaluate the data instances and determines whether to include the data instances in the training set or not. For example, the data augmentation can be used to grab the appearance of blood scene (e.g., the style) and mix it with the content of another that has soft tissues exposed. Using this technique, a surgical scene-like effect can be produced to make the training model even more suitable for real application.

Figure 20:
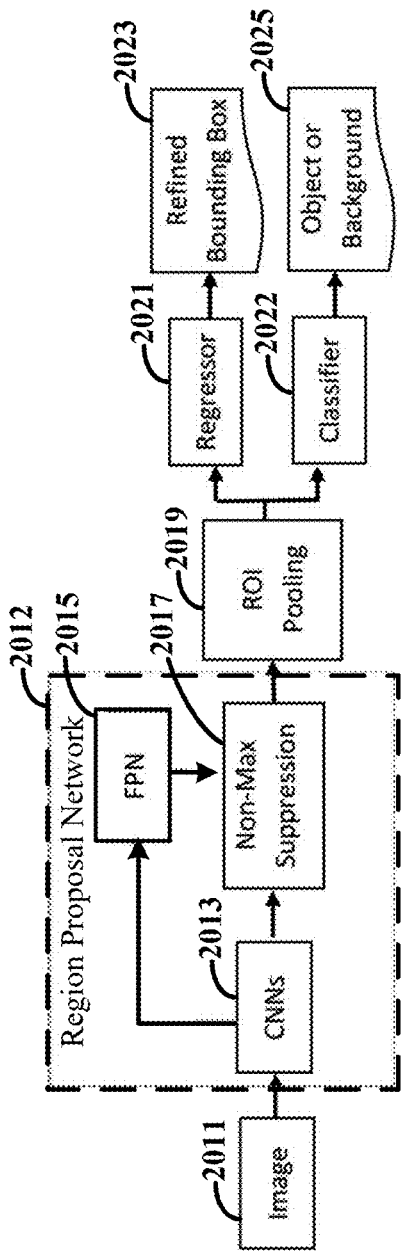
FIG. 20 illustrates an example object detection module in accordance with various embodiments.

FIG. 20 illustrates an example of an object detection module, in accordance with various embodiments. The object detection module can include a Faster R-CNN, which includes a two-stage framework. The first stage, region proposal network (RPN) 2012, is used to scans the image and generates multiple proposals for the areas likely to contain an object. The second stage, ROI pooling, is used to classify the proposals and generate bounding boxes. Unlike other computationally expensive versions of region-based CNNs, by using selective search to generate region proposals, the object detection module can share convolutional features across proposals with a deep net at test-time and make the marginal cost for computing proposals very small. By intelligently ranking region boxes (also called anchors), RPN 2012 can propose the ones most likely containing objects.

In RPN 2012, a function including backbone CNNs 2013 based on Residual Neural Network (ResNet) 101 is used as a feature extractor on the input image 2011. Although ResNet 101 has slightly higher computational load than other CNNs backbone such as ResNet 50, Visual Geometric Group (VGG) 16, Inception, MobileNet, and/or Dense Convolution Network (DenseNet), and can give significantly improved results.

Additionally in the RPN 2012, rather than generating a feature map in a single layer in the standard backbone, a feature pyramid network (FPN) 2015 is constructed to represent object features at multiple scales to help improve performance. FPN 2015 allows features at every level to have access from lower level features, such as edges and corners at its early layers, to higher level features, such as tissue structures and objects at its later layers. The image passing through the backbone network is converted to a set of feature maps as inputs for the next stage.

In the pipeline, the RPN 2012 scans the image 2011 with different sizes of anchors in a sliding-window fashion and finds areas that may contain objects. The RPN 2012 can generate two outputs for each anchor. One is the anchor class implying the area for foreground or background. The other is the anchor confidence indicating the probability of the object inside the box. The function of the non-max suppression sub-module 2017 in the RPN 2012 selects the positive anchors with higher confidence score that are likely to contain objects and refines the locations and sizes to be more centered and fit over the object. If several anchors overlap too much, the one with the highest foreground score is kept and the rest are discarded.

After RPN 2012, many proposed regions with different sizes are obtained. Different sized regions have different sized feature maps, which can be difficult to work with in an efficient structure. ROI pooling, at 2019, can be used to crop a part of a feature map and resize it to a fixed size. With the fixed ROI pooling outputs as inputs, a plurality of choices can be passed through the architecture in the second stage. Just like the RPN 2012, the second part of the deep neural network also generates two outputs for each ROI by the Classifier 2022 and the Regressor 2021, respectively. But unlike the RPN, which has two classes (foreground/background), the Classifier 2022 in this network is deeper and has the capacity to classify regions, at 2025, to specific classes of features, such as nerve, vessel, organ, etc. The ROI also generate a background class, which causes the ROI to be discarded. The function of the Regressor 2021 is similar to the RPN, and its purpose is to further refine the location and size of the bounding box to encapsulate the object, at 2023. The final anchors output by the refined bounding box step, at 2023, can restore its size and location corresponding to the original image.

Figures 21A, 21B, 21C, 21D:
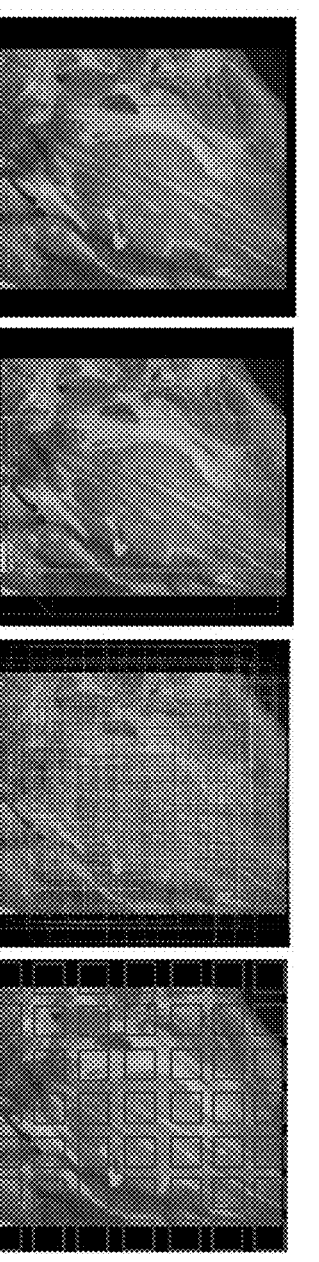
FIGS. 21A-21D illustrate images having anchors generated, in accordance with various embodiments.

FIGS. 21A-21D illustrate images having anchors generated, in accordance with various embodiments. For example, the anchors can be generated using the object detection module illustrated by FIG. 20. More specifically, FIGS. 21A-21D show examples of anchors/boxes generated from the object detection module, where FIG. 21A has a simplified view of input anchors, FIG. 21B shows a view of anchors output from the RPN, FIG. 21C shows refined anchors from the Regressor, and FIG. 21D shows the final anchor with the highest score.

Figure 22A:
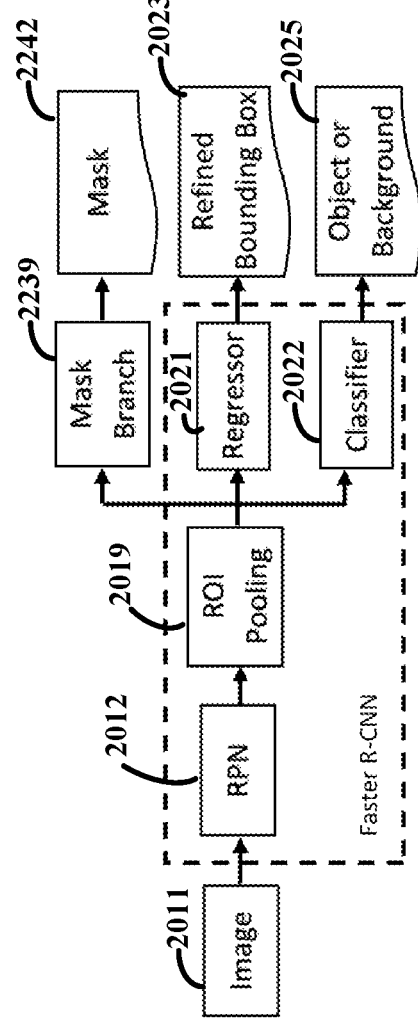
FIGS. 22A-22C illustrate an example object segmentation module, in accordance with various embodiments.
Figures 22B, 22C:
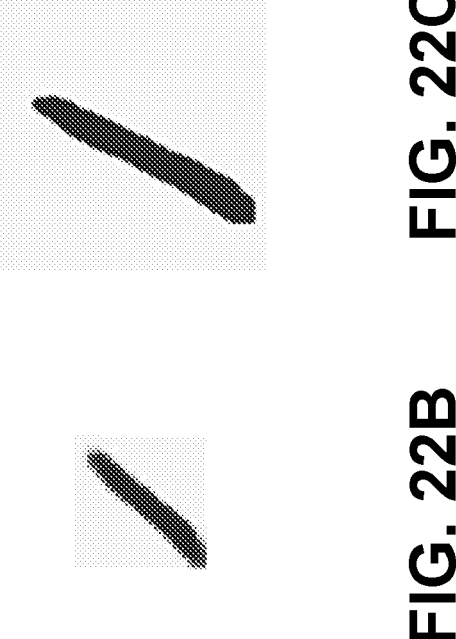

FIG. 22A-22C illustrate an example object segmentation module, in accordance with various embodiments. This module can include or be based on Mask-RCNN which extends the Faster-RCNN architecture with an additional mask network for object segmentation.

FIG. 22A shows an example of the object segmentation module. The object segmentation module is shown in connection with the object detection module previously described by FIG. 20 including the input image 2011 which is processed using the RPN 2012, ROI pooling 2019, the Regressor 2021, and Classifier 2022, which results in the classification of object or background and redefined bounding box, as previously described. The object segmentation module adds a mask branch 2239. The mask branch 2239 is a convolutional network that takes the positive regions selected by the ROI pooling 2019 and generates masks 2242 for them. The generated masks 2242 are low resolution, in this case 28×28 pixels. The masks 2242 can be soft masks, represented by float numbers, such that the masks 2242 can hold more details than binary masks. The small mask size also assist in keeping the mask branch light. During training, the ground-truth masks can be scaled down to 28×28 to compute the loss. During inferencing, the predicted masks can be scaled up to the size of the ROI bounding box 2023 and that gives the final masks, one per object as shown in FIGS. 22B-22C as examples. In Mask-RCNN, an ROI alignment for feature maps is also been added that replaces the somewhat imprecise ROI pooling operation used in Faster-RCNN to allow more accurate object segmentation masks to be constructed. This ROI alignment is achieved by sampling the feature map at different points and applying a bilinear interpolation to minimize information loss. Finally, mask and class predictions are decoupled. The mask network head predicts the mask independently from the network head predicting the class. The multitask loss function summing them up, such as $L_{total} = L_{class} + L_{boundingbox} + L_{mask}$ being used as the final performance measurement.

FIGS. 22B and 22C illustrates example segmentation masks. FIG. 22B is an example mask used for ground truth and FIG. 22C is an example mask for prediction.

Figure 23:
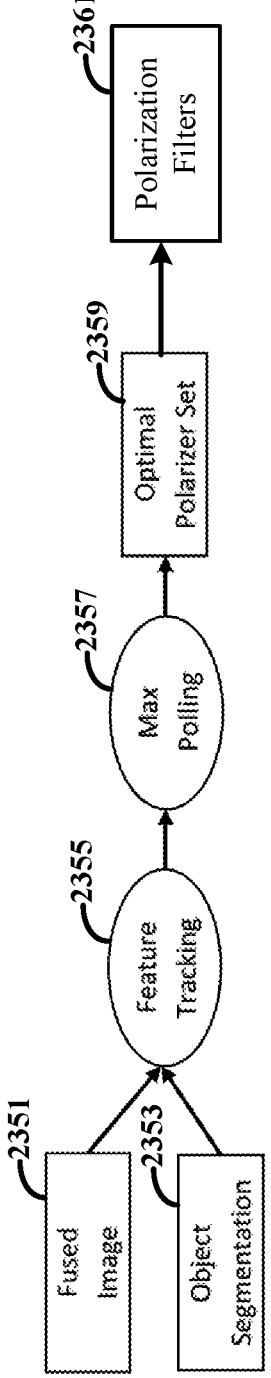
FIG. 23 illustrates an example feedback module, in accordance with various embodiments.

FIG. 23 illustrates an example feedback module, in accordance with various embodiments. The multi-polarization imaging process in default mode for both visible and NIR spectrums can utilize all available polarization angles to produce images. This process can create large amounts of data but not all polarized images contain equivalent and/or desirable information that is used for processing into the pipeline for the optimized view. Different objects can use various subsets of polarization angles, even the suitable polarizers for the same object can change over the time as the image sensor position changes. The feedback control module is used with the control of continuously imaging apparatus to optimize the polarization selection process with most relevant polarization angles, such as the angles relevant to the tissue objects for subsequence image processing.

Based on the outcome of object segmentation 2353, the objects or features in the fused image 2351 can be further analyzed with respect to shape features including orientation, size, aspect ratio, surface texture, compactness, sphericity and concavity, at 2355. The feedback module, using the feature track, can compute these features for the detected objects and track any changes from the sensor motion. These features are also used to support the max polling process, at 2357. Given the fused image, the max polling function can compare the energy of the object with each polarized frame and select the most significant frames contributing to the energy of the fused image 2351. The energy, as previously described, refers to or includes a response of a pixel region, which can be obtained using gradient-based filtering. The output of this function, at 2359, can be the optimal polarizer set that can be used to guide the imaging sensor, such as being used to control the polarization filters 2361 (by the control circuitry of the imaging apparatus). Once the feature tracking has changed, at 2353, the polarization process can go back to the default mode and activate the max polling, at 2357, to operate again. This feedback control loop allows the image sensor to dynamically choose the suitable polarizers at any given time corresponding to the view.

To illustrate the concept, focus is placed on nerve tissue as nerve tissue is challenging soft tissue to process. The dataset used for experiments is collected from rabbit tissue samples that is imaged by an imaging apparatus consistent with FIG. 1, which includes 165 polarized visible and NIR images covering different nerve portions, but primarily in spinal regions. The corresponding annotations for each individual nerve are detected by a human for each image. VGG Image Annotator is used to make labeled data complying with MSCOCO format. Of the 138 images in the dataset, 108 images can be used for training and validating the model and 30 images are held out for testing.

For the machine learning experiments described herein, a Mask-RCNN model is implemented based on the open-source libraries Keras and Tensorflow. With transfer learning, the model is initialized using weights obtained from pretraining on the MSCOCO dataset rather than training the network end-to-end from the start. The model is trained with the network layers in three stages: first, training only the network heads, which are randomly initialized, then training the upper layers of the network (from stage 4 and up in the ResNet model), and then reducing the learning rate by a factor of 10 and training end to end. In total 50 epochs can be trained using stochastic gradient descent with momentum of 0.9, starting with a learning rate of 0.001 and ending with a learning rate of 0.0001. Although longer and shorter training times can be experimented with, additional training may not lead to any noticeable improvement and fewer epochs led to underfit. A batch size of forty on a single NVIDIA Titan 1080 GPU is used. As a result, the Mask R-CNN model and parameters as described above obtains an average mask intersection over union (IoU) of 72.8% on the validation dataset.

Figure 24:
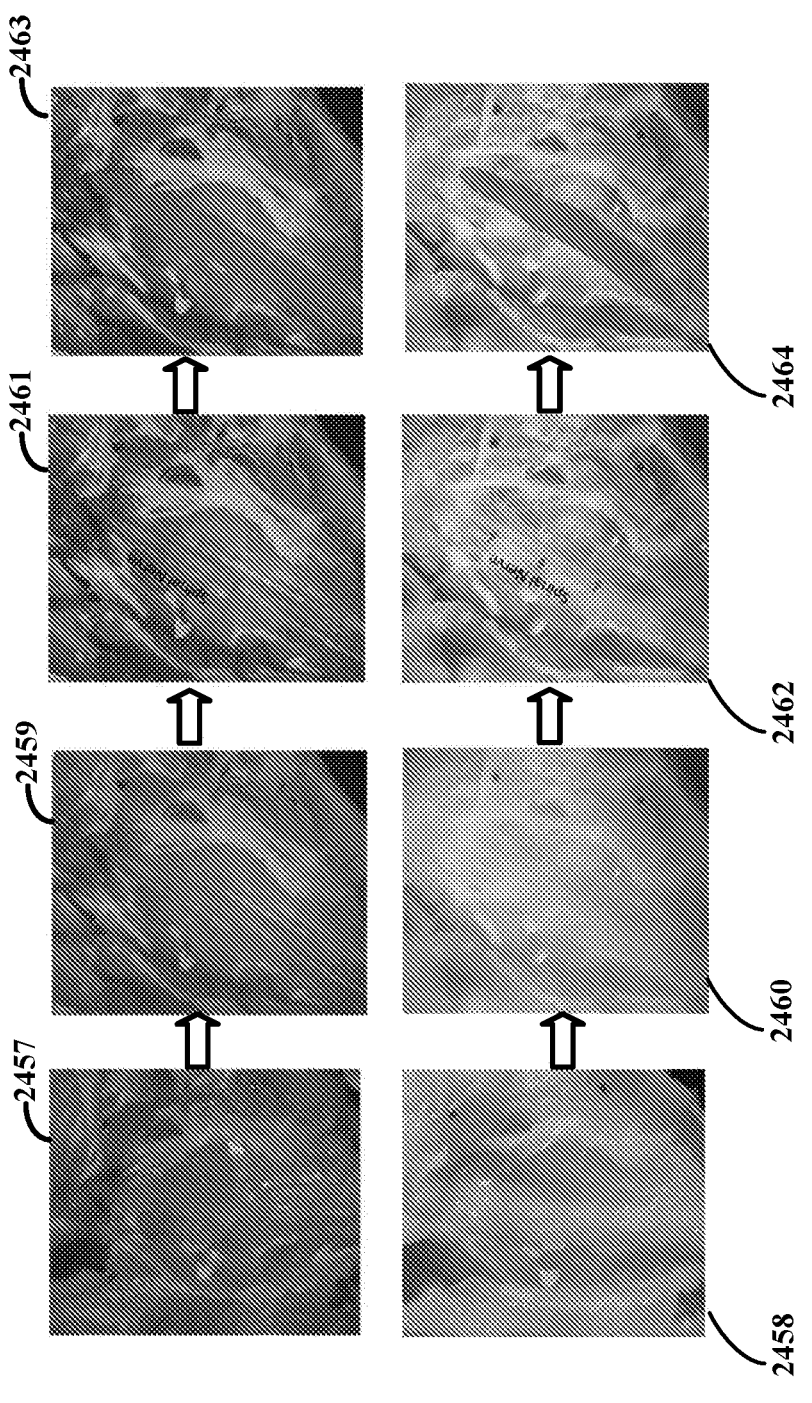
FIG. 24 illustrates example series of polarized images with image enhancement and detection of features, in accordance with various embodiments.

FIG. 24 illustrates an example series of polarized images with image enhancement and detection of features, in accordance with various embodiments. More specifically, FIG. 24 shows images 2457, 2458, 2459, 2460, 2461, 2462, 2463, and 2464 of experimental results of tissue sample imaged with and without polarization. The image enhancement and alignment algorithms follow to process both visible and NIR images shown to further contrast improvement. These enhanced images are passed for post-processing, which can include machine learning inference that detects the nerve location and segments the regions. More specifically, image 2457 is a non-polarized VIS image, image 2459 is a polarized VIS image, image 2461 is an enhanced (or post-processed) polarized VIS image, and image 2463 is a segmented nerve is the enhanced polarized VIS image. Image 2458 is a non-polarized NIR image, image 2460 is a polarized NIR image, image 2462 is an enhanced (or post-processed) polarized NIR image, and image 2464 is a segmented nerve is the enhanced polarized NIR image.

Oftentimes during surgery, blood is present over the tissue surface, which can significantly degrade the visibility of soft tissues. Another experiment is conducted to mimic this condition with red ink.

Figure 25:
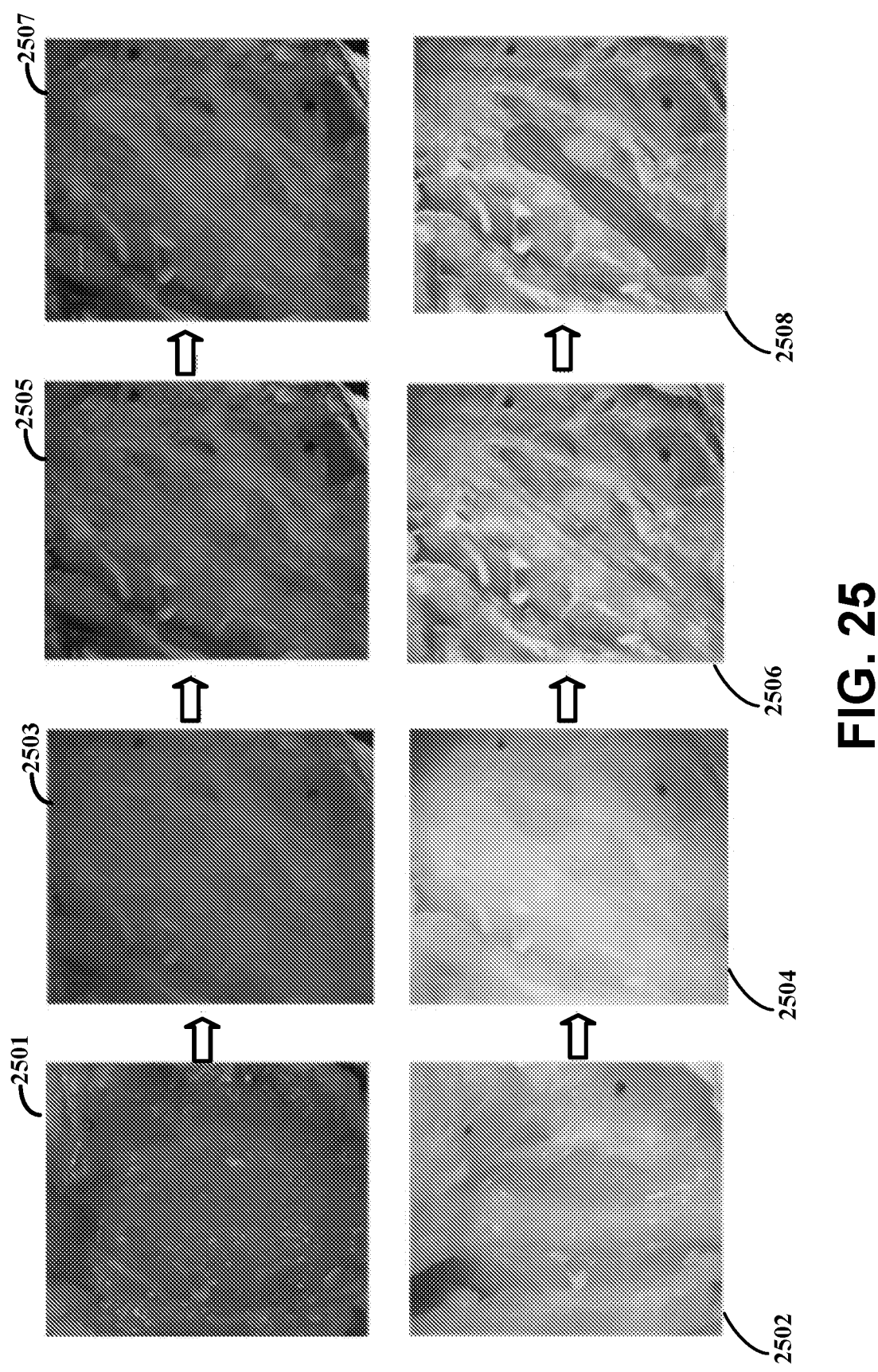
FIG. 25 illustrates examples series of polarized images through red ink with image enhancement and detection of features, in accordance with various embodiments.

FIG. 25 illustrates examples series of polarized images through red ink with image enhancement and detection of features, in accordance with various embodiments. FIG. 25 shows images 2501, 2502, 2503, 2504, 2505, 2506, 2507, 2508 of experimental results of tissue sample imaged with and without polarization with blood over the tissue surface. More specifically, image 2501 is a non-polarized VIS image, image 2503 is a polarized VIS image, image 2505 is an enhanced (or post-processed) polarized VIS image, and image 2507 is a segmented nerve is the enhanced polarized VIS image. Image 2502 is a non-polarized NIR image, image 2504 is a polarized NIR image, image 2506 is an enhanced (or post-processed) polarized NIR image, and image 2508 is a segmented nerve is the enhanced polarized NIR image. As shown, the NIR image has less contrast degradation than the visible image after polarization. This explains advantage of multispectral imaging because the near-infrared part of the electromagnetic spectrum can have better penetration than visible for human tissues (or other types of tissues).

Figure 26:
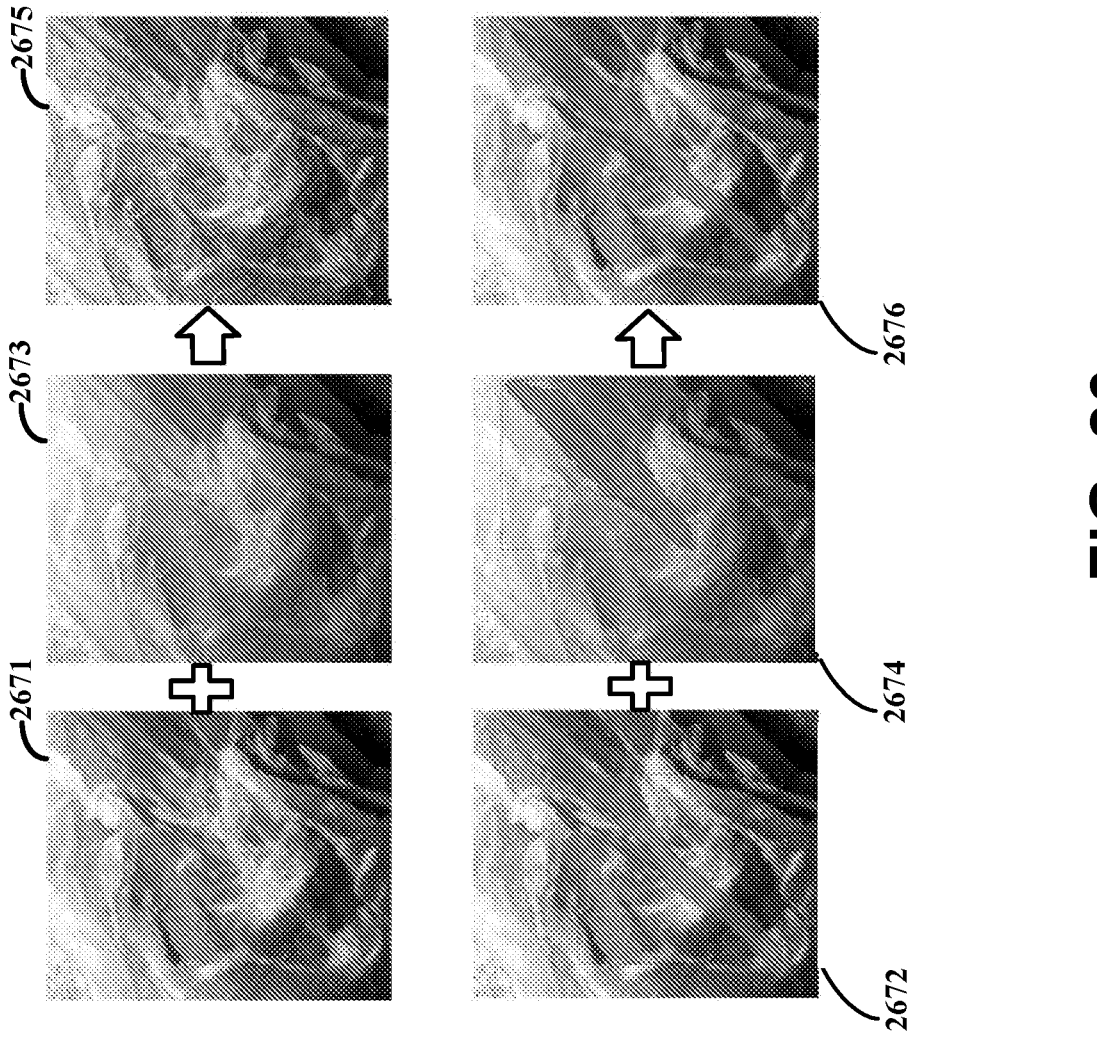
FIG. 26 illustrates example polarized images with fusion of enhancement and detection for features, in accordance with various embodiments.

FIG. 26 illustrates example polarized images with fusion of enhancement and detection for features. More specifically, FIG. 26 illustrates fusion results from both visible and NIR for image contrast enhancement and object segmentation are demonstration, where neither the visible nor the NIR image alone provides complete information but the combined image does. This combined result can be rendered to surgeons as the final output from the system. Image 2671 is an enhanced polarized VIS image, image 2673 is an enhanced polarized NIR image, and image 2675 is fused image with nerve enhanced. Image 2672 is an enhanced polarized VIS image with nerve detected, image 2674 is an enhanced polarized NIR image with nerve detected, and image 2676 is fused image with nerve detected.

In accordance with various experimental embodiments, e a multispectral polarized imaging system with advanced image processing and machine learning or artificial intelligence is used to show improvement of visual quality and detectability of nerve tissues. The vision system with polarized imagery can be developed as add-on module easily integrated and adapted with existing endoscopes to be practically used during surgery to help surgeons with the challenging tasks of discriminating the nerves. The functions developed here can also be used as a framework for identifying other soft tissues such as blood vessels, lymphatic vessels and tumors without much modification or customization. After this, the efficacy and performance of modules can be explored for a range of tasks such as correlating imagery and bio-signals to monitor tissue health condition and to give an early damage warning for decision support.

In a number of specific embodiments, the machine learning can include the use of additional inputs. The combined inputs can include visible light image frames, NIR image frames, and ultrasonic information. In various embodiments, additional inputs can be used, such as ECG/EMG, MEP, SSEP and/or other physiological inputs (e.g., vibration, temperature, pressure) which can be used for neuromonitoring. A pattern can be observed from these signals, such as in time or frequency domain, which can be learned over time and used to monitor nerve health condition. The postprocessing, in such examples, can include receiving the inputs from the plurality of sensors. The plurality of sensors including an imaging apparatus, as described herein, an ultrasonic source, and one or more sources providing the physiological inputs. The input data in preprocessed, such as by segmenting the various input, and then fused to together to combine the signals. The combined signals are processed using the above-described modules, which are used to provide diagnosis results.

More specifically, machine learning may be used to learn and/or predict nerve heath using multiple inputs including the physiological inputs and the VIS, NIR, and/or US images and/or information. The multiple inputs, including physiological inputs, are converted and combined to a two-dimensional (2D) like image (e.g., frequency or intensity verses time) and applied to machine learning algorithms for training a model to monitor and/or predict the nerve health. Machine learning can be used to learn the correlation between nerve responses with external electrical pulses (usually a long observation time) from normal and ill patients or other mammals. The model can be used for interference with a number of electrical pulses and the actual nerve responses are compared with model to identify differences, such as whether the responses are normal or abnormal.

Various embodiments are implemented in accordance with the underlying Provisional Application (Ser. No. 62/812,413), entitled "Methods for Real-Time Soft Tissue Visualization and Identification," filed Mar. 1, 2019, and which includes Attachment A and Attachment B, and Provisional Application (Ser. No. 62/812,405), entitled "Algorithms for Image Enhancement and Object Detection for Soft Tissues," filed Mar. 1, 2019 and which includes Attachment A, to which benefit is claimed and which are both fully incorporated herein by reference for their general and specific teachings, and including the respective Attachments. For instance, embodiments herein and/or in the provisional application can be combined in varying degrees (including wholly). Reference can also be made to the experimental teachings and underlying references provided in the underlying Provisional Applications. Embodiments discussed in the Provisional Applications are not intended, in any way, to be limiting to the overall technical disclosure, or to any part of the claimed disclosure unless specifically noted.

Although described or shown with respect to one embodiment, the features and elements so described or shown can apply to other embodiments. It will also be appreciated by those of skill in the art that references to a structure or feature that is disposed "adjacent" another feature can have portions that overlap or underlie the adjacent feature. Additionally, although various embodiments describe imaging of a sample, embodiments are not so limited and can include imaging of whole or partial objects, such as for use in three-dimensional imaging or printing and/or for in-field images of particular objects and/or portions thereof.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and can be abbreviated as "/".

The skilled artisan would recognize that various terminology as used in the Specification (including claims) connote a plain meaning in the art unless otherwise indicated. As examples, the Specification describes and/or illustrates aspects useful for implementing the claimed disclosure by way of various circuits or circuitry which can be illustrated as or using terms such as blocks, modules, device, system, unit, controller, and/or other circuit-type depictions (e.g., reference numerals 431-436 of FIG. 4 depict a block/module as described herein). Such circuits or circuitry are used together with other elements to exemplify how certain embodiments can be carried out in the form or structures, steps, functions, operations, activities, etc. For example, in certain of the above-discussed embodiments, one or more modules are discrete logic circuits or programmable logic circuits configured and arranged for implementing these operations/activities, as can be carried out in the approaches shown in FIG. 5-6. In certain embodiments, such a programmable circuit is one or more computer circuits, including memory circuitry for storing and accessing a program to be executed as a set (or sets) of instructions (and/or to be used as configuration data to define how the programmable circuit is to perform), and an algorithm or process as described at FIG. 10 is used by the programmable circuit to perform the related steps, functions, operations, activities, etc. Depending on the application, the instructions (and/or configuration data) can be configured for implementation in logic circuitry, with the instructions (whether characterized in the form of object code, firmware or software) stored in and accessible from a memory (circuit).

Various embodiments described above, can be implemented together and/or in other manners. One or more of the items depicted in the present disclosure can also be implemented separately or in a more integrated manner, or removed and/or rendered as inoperable in certain cases, as is useful in accordance with particular applications. In view of the description herein, those skilled in the art will recognize that many changes can be made thereto without departing from the spirit and scope of the present disclosure.

What is claimed is:

1. An apparatus comprising:

a light source configured to output a light beam along an optical pathway;

a first polarizer coupled to the light source and configured to pass first polarized light from the output light beam and toward a sample along the optical pathway;

an image sensor, including circuitry, configured to collect light reflected from the sample in response to the passed first polarized light;

a second polarizer arranged along the optical pathway between the sample and the image sensor and configured to pass second polarized light from the light reflected from the sample in response to the passed first polarized light and toward the image sensor, wherein the first and second polarizers are linear and cross each other;

a filter arranged along the optical pathway and configured to selectively pass the reflected light in a visible light range and near infrared range (NIR) light range toward the image sensor;

control circuitry configured and arranged with the image sensor to image the sample by:

causing the first polarizer and the second polarizer to adjust to different polarization angles with respect to one another; and collecting image data of the sample from the light reflected while the first and second polarizers are at the different polarization angles with respect to one another and while the filter selectively passes the visible light and the NIR light ranges of the second polarized light; and processing circuitry configured to:

generate a plurality of NIR image frames and a plurality of visible light image frames from the image data collected while the first and second polarizers are at the different polarization angles;

revise the image data including:

adjusting contrast of the plurality of NIR image frames and the plurality of visible light image frames by redistributing light intensity values; and aligning the plurality of NIR image frames with the plurality of visible light image frames by identifying keypoints in the respective image frames and shape descriptors of features, sorting the keypoints based on the shape descriptors, and aligning pixels within the respective image frames using the sorted keypoints; and fuse the plurality of NIR image frames and the plurality of visible light image frames into a single composite image based on the revised image data.

2. The apparatus of claim 1, wherein:

the first polarized light and the second polarized light are associated with a slant with respect to one another, the sample includes a tissue sample, and the control circuitry is configured to cause the first polarizer and the second polarizer to adjust to the different polarization angles such that the first polarized light and second polarized light are crossed with each other and for the different polarization angles, resulting in optical reflections of birefringence from portions of the tissue sample to be focused or discriminated when aligned to a polarization of collimated incident light.

3. The apparatus of claim 1, wherein the control circuitry is configured to collect the image data by causing the filter to selectively pass the visible light and the NIR light and collecting a plurality of image frames of the sample while the first and second polarizers are at the different polarization angles with respect to one another, while the filter selectively passes the visible light range and while the filter selectively passes the NIR light range, wherein the plurality of NIR image frames are generated from the NIR light range of 715 nanometers (nm) to 2500 nm and the plurality of visible light image frames are generated from the visible light range of 400 nm to 700 nm.

4. The apparatus of claim 1, wherein the control circuitry is configured to collect the image data by collecting a sequential order of image frames including the plurality of NIR image frames and the plurality of visible light image frames responsive to the first and second polarizers being at the different polarization angles with respect to one another, and while the filter selectively passes both the NIR and visible light ranges.

5. The apparatus of claim 1, wherein the processing circuitry is configured to adjust the contrast of the plurality of NIR image frames and the plurality of visible light image frames by redistributing the light intensity values, applying a bilateral filter and combining the redistributed light intensity values with the bilateral filtered space.

6. The apparatus of claim 1, wherein the processing circuitry is further configured to identify which of the different polarization angles of the first and second polarizers results in areas of interest of the sample being in focus, and to provide feedback to the control circuitry to revise the image data based on the areas of interest being in focus.

7. The apparatus of claim 1, wherein the filter includes a first bandpass filter configured to selectively pass visible light and a second bandpass filter configured to selectively pass NIR wavelengths.

8. The apparatus of claim 7, further including a motorized rotator arranged with the first and second bandpass filters, and the control circuitry is further configured and arranged to selectively rotate the motorized rotator such that one of the first and second bandpass filters are arranged in the optical pathway to selectively pass one of the visible and NIR wavelengths.

9. The apparatus of claim 1, wherein the filter includes a bandpass filter configured to selectively block incident light and a color filter array configured to capture NIR, red, green, and blue channels at the same time.

10. The apparatus of claim 9, wherein the control circuitry is configured to collect the image data by capturing first image data using collimated incident light as generated by the first and second polarizer, and by capturing second image data using non-polarized light from the light source, the captured first and second image data including the plurality of NIR image frames and the plurality of visible light image frames of the sample which are captured at the same time.

11. The apparatus of claim 1, further including a first motorized rotator coupled to the first polarizer and a second motorized rotator coupled to the second polarizer, wherein the control circuitry is further configured to selectively rotate the first and second motorized rotators such that the first and second polarizers are at the different polarization angles.

12. The apparatus of claim 11, wherein the first and second polarizers each include a plurality of polarized filters arranged on the first and second motorized rotators to provide the different polarization angles and each include an all-pass filter arranged on the first and the second motorized rotators, the all-pass filters being configured to pass light of all polarizations.

13. The apparatus of claim 1, wherein the apparatus includes an endoscope having a distal end, a proximal end, and a rigid tube arranged between the distal end and the proximal end, wherein:

the image sensor is coupled to the distal end, and the distal end is arranged with the rigid tube to provide light reflected from the sample to the image sensor;

the light source is coupled to the rigid tube via another tube between the distal end and the proximal end and to provide the light beam along the optical pathway;

the first polarizer is positioned proximal to the light source, the first polarizer including a filter that is sized according to illumination channels associated with the other tube and the light source;

the second polarizer is positioned proximal to the image sensor along the rigid tube, the second polarizer including a filter that is sized according to an imaging channel associated with the rigid tube and the image sensor; and the proximal end is configured to couple to an elongated flexible tube.

14. The apparatus of claim 1, wherein the processing circuitry is in communication with the control circuitry and configured to:

revise the image data to improve the contrast of areas of interest in the image data of the sample, and thereby increasing salient features of the areas of interest;

identify locations of the areas of interest in the revised image data by the aligning of the image data including the plurality of NIR image frames with the plurality of visible light image frames and identifying objects and object segments in the image data; and fuse the plurality of NIR image frames and the plurality of visible light image frames into the single composite image of the sample based on the revised image data and the identified locations of the areas of interest.

15. A method comprising:

adjusting a first polarizer and a second polarizer to different polarization angles with respect to one another, wherein the first and second polarizers are linear and cross each other while at each of the different polarization angles:

outputting a light beam along an optical pathway using a light source;

passing, using the first polarizer, first polarized light from the output light beam and toward a sample along the optical pathway;

reflecting light from the sample responsive to the first polarized light;

passing second polarized light, using the second polarizer, from the light reflected from the sample and toward an image sensor;

selectively passing the second polarized light in a visible light range and a near infrared range (NIR) light range toward the image sensor;

collecting, using the image sensor, image data of the sample from the light reflected while the first and second polarizers are at the different polarization angles with respect to one another and while the visible light and the NIR light ranges of the second polarized light are selectively passed;

generating a plurality of NIR image frames and a plurality of visible light image frames from the image data collected while the first and second polarizers are at the different polarization angles;

revising the image data including:

adjusting contrast of the plurality of NIR image frames and the plurality of visible light image frames by redistributing light intensity values; and aligning the plurality of NIR image frames with the plurality of visible light image frames by identifying keypoints in the image frames and shape descriptors of features, sorting the keypoints based on the shape descriptors, and aligning pixels within respective image frames using the sorted keypoints; and fusing the plurality of NIR image frames and the plurality of visible light image frames into a single composite image using the revised image data.

16. The method of claim 15, wherein fusing the plurality of NIR image frames and the plurality visible light image frames into the single composite image includes:

combining the plurality of NIR image frames to form a composite NIR image;

combining the plurality of visible light image frames to form a composite visible light image; and combining the composite NIR image and the composite visible light image to form the single composite image.

17. The method of claim 15, wherein adjusting the first polarizer and the second polarizer to the different polarization angles results in optical reflections of birefringence from portions of the sample to be focused or discriminated when aligned to polarization of collimated incident light, and the method further including identifying which of the different polarization angles of the first and second polarizers results in an area of interest of the sample being in focus.

18. The method of claim 15, wherein:

adjusting the contrast of the plurality of visible light image frames and the plurality of NIR image frames to revise the image data further includes computing histograms, redistributing the light intensity values based on the histograms, applying a bilateral filter, and combining the redistributed light intensity values with the bilateral filtered space; and aligning the plurality of NIR image frames with the plurality of visible light image frames further includes identifying the keypoints in the image frames and the shape descriptors of features, using the shape descriptors to sort the keypoints, and estimating a homography using the sorted keypoints and to align pixels within respective image frames.

19. The method of claim 15, wherein collecting the image data includes:

causing a filter to selectively pass the visible light range and the NIR light range; and collecting a plurality of image frames of the sample while the first and second polarizers are at the different polarization angles with respect to one another, while the filter selectively passes the visible light range and while the filter selectively passes the NIR light range.

20. The method of claim 15, wherein:

collecting the image data includes collecting a sequential order of image frames responsive to the first and second polarizers being at the different polarization angles with respect to one another, and while a filter selectively passes both the NIR and visible light ranges; and adjusting the contrast of the plurality of NIR image frames and the plurality of visible light image frames includes redistributing the light intensity values, applying a bilateral filter, and combining the redistributed light intensity values with the bilateral filtered space.

21. The method of claim 15, wherein collecting the image data includes capturing first image data using collimated incident light as generated by the first and second polarizer and capturing second image data using non-polarized light from the light source, the captured first and second image data including video of the sample.

* * * * *